(12) United States Patent
De Boer et al.

(10) Patent No.: US 7,547,783 B2
(45) Date of Patent: *Jun. 16, 2009

(54) TRANSITION METAL COMPLEXES

(75) Inventors: Eric Johannes Maria De Boer, Amsterdam (NL); Harry Van Der Heijden, Amsterdam (NL); Quoc An On, Amsterdam (NL); Johan Paul Smit, Amsterdam (NL); Arie Van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 504 days.

This patent is subject to a terminal disclaimer.

(21) Appl. No.: 11/088,023

(22) Filed: Mar. 23, 2005

(65) Prior Publication Data

US 2005/0215792 A1    Sep. 29, 2005

(30) Foreign Application Priority Data

Mar. 24, 2004    (EP)    ................... 04251688

(51) Int. Cl.
*C07F 15/00*    (2006.01)
*B01J 31/22*    (2006.01)
*C08F 4/80*    (2006.01)

(52) U.S. Cl. .................. 546/10; 502/155; 502/167; 526/161; 526/171; 526/172; 526/348; 546/145

(58) Field of Classification Search .............. 546/10, 546/145; 502/155, 167; 526/161, 171, 172, 526/348
See application file for complete search history.

(56) References Cited

U.S. PATENT DOCUMENTS

| | | | |
|---|---|---|---|
| 4,728,583 A | 3/1988 | Yamazaki et al. | 428/690 |
| 4,822,911 A | 4/1989 | Fried | 560/205 |
| 4,912,333 A | 3/1990 | Roberts et al. | 250/487.1 |
| 4,944,026 A | 7/1990 | Arakawa et al. | 250/484.1 |
| 5,151,604 A | 9/1992 | Kohda et al. | 250/484.1 |
| 5,318,935 A | 6/1994 | Canich et al. | 502/117 |
| 5,607,774 A | 3/1997 | Dahlquist et al. | 428/447 |
| 5,726,115 A | 3/1998 | Horton et al. | 502/152 |
| 5,830,629 A | 11/1998 | Vizard et al. | 430/523 |
| 5,852,145 A | 12/1998 | McLain et al. | 526/133 |
| 5,888,647 A | 3/1999 | Yamane | 428/338 |
| 5,905,014 A | 5/1999 | Van de Bergh | 430/139 |
| 5,932,670 A | 8/1999 | Köppl et al. | 526/161 |
| 5,955,555 A | 9/1999 | Bennett | 526/133 |
| 6,002,034 A | 12/1999 | McLain et al. | 556/34 |
| 6,063,881 A | 5/2000 | Bennett | 526/161 |
| 6,103,946 A | 8/2000 | Brookhart, III et al. | 585/523 |
| 6,150,482 A | 11/2000 | Brookhart, III et al. | 526/161 |
| 6,214,761 B1 | 4/2001 | Bennett | 502/117 |
| 6,232,259 B1 | 5/2001 | Ittel et al. | 502/155 |
| 6,265,500 B1 | 7/2001 | Debras | 526/65 |
| 6,291,733 B1 | 9/2001 | Small et al. | 585/512 |
| 6,310,153 B2 | 10/2001 | Ittel et al. | 526/172 |
| 6,395,668 B1 | 5/2002 | van Baar et al. | 502/123 |
| 6,407,188 B1 | 6/2002 | Guan et al. | 526/113 |
| 6,414,098 B1 | 7/2002 | Engehausen et al. | 526/161 |
| 6,417,305 B2 | 7/2002 | Bennett | 526/161 |
| 6,417,364 B1 | 7/2002 | Lenges | 546/12 |
| 6,423,848 B2 | 7/2002 | Bennett | 546/329 |
| 6,432,862 B1 | 8/2002 | Bennett | 502/117 |
| 6,441,117 B1 | 8/2002 | Cameron | 526/352 |
| 6,451,939 B1 | 9/2002 | Britovsek et al. | 526/161 |
| 6,455,660 B1 | 9/2002 | Clutton et al. | 526/352 |
| 6,458,672 B1 | 10/2002 | Henley et al. | 438/478 |
| 6,458,739 B1 | 10/2002 | Kimberley et al. | 502/155 |
| 6,458,905 B1 | 10/2002 | Schmidt et al. | 526/172 |
| 6,461,994 B1 | 10/2002 | Gibson et al. | 502/155 |
| 6,462,152 B1 | 10/2002 | Berardi et al. | 526/75 |
| 6,462,155 B1 | 10/2002 | Okuda | 526/161 |
| 6,465,386 B1 | 10/2002 | Maddox et al. | 502/155 |
| 6,472,341 B1 | 10/2002 | Kimberley et al. | 502/155 |
| 6,479,601 B1 | 11/2002 | Kerns et al. | 526/161 |

(Continued)

FOREIGN PATENT DOCUMENTS

CN    1268106    9/2000

(Continued)

OTHER PUBLICATIONS

Britovsek G J P et al: "Iron-Catalyzed Polyethylene Cahin Growth on Zinc: Linear alpha-Olefins with a Poisson Distribution" Angewandte Chemie. International Edition, Wiley-VCH, Weinheim, DE, vol. 41, No. 3, Jan. 29, 2002, pp. 489-491, XP002286464.

(Continued)

*Primary Examiner*—Charanjit S Aulakh

(57) ABSTRACT

A transition metal complex which is a bis-arylimine pyridine $MX_n$ complex or a [bis-arylimine pyridine MXp+][NC-]q complex comprising a bis-arylimine pyridine ligand and M is a transition metal atom; n matches the formal oxidation state of the transition metal atom M; X is halide, optionally substituted hydrocarbyl, alkoxide, amide, or hydride; NC- is a non-coordinating anion; and p+q matches the formal oxidation state of the transition metal atom M. The transition metal complexes of the present invention, their complexes with non-coordinating anions and catalyst systems containing such complexes have good solubility in non-polar media and chemically inert non-polar solvents especially aromatic hydrocarbon solvents. The catalyst systems can be used for a wide range of (co-)oligomerization, polymerization and dimerization reactions.

24 Claims, No Drawings

U.S. PATENT DOCUMENTS

| | | | |
|---|---|---|---|
| 6,489,497 B1 | 12/2002 | Brookhart, III et al. | 556/138 |
| 6,521,329 B2 | 2/2003 | Aylward et al. | 428/212 |
| 6,534,691 B2 | 3/2003 | Culver et al. | 585/527 |
| 6,545,108 B1 | 4/2003 | Moody et al. | 526/161 |
| 6,548,672 B1 | 4/2003 | Gibson et al. | 546/12 |
| 6,555,723 B2 | 4/2003 | Schiffino | 585/521 |
| 6,559,091 B1 | 5/2003 | Moody et al. | 502/167 |
| 6,559,252 B1 | 5/2003 | Horton et al. | 526/160 |
| 6,583,237 B1 | 6/2003 | Imuta et al. | 526/89 |
| 6,605,677 B2 | 8/2003 | Lavoie et al. | 526/161 |
| 6,677,267 B2 | 1/2004 | Berardi et al. | 502/155 |
| 6,683,141 B1 | 1/2004 | Gibson et al. | 526/161 |
| 6,683,187 B2 | 1/2004 | De Boer et al. | 546/345 |
| 6,706,891 B2 | 3/2004 | Ponasik, Jr. et al. | 548/523 |
| 6,710,006 B2 | 3/2004 | De Boer et al. | 502/155 |
| 6,740,715 B2 | 5/2004 | Brookhart, III et al. | 526/161 |
| 6,825,297 B1 | 11/2004 | Devore et al. | 526/172 |
| 6,838,540 B2 | 1/2005 | Mitani et al. | 526/348 |
| 7,037,988 B2* | 5/2006 | De Boer et al. | 526/161 |
| 7,049,442 B2 | 5/2006 | De Boer et al. | 546/268.1 |
| 7,053,020 B2* | 5/2006 | De Boer et al. | 502/155 |
| 7,304,159 B2* | 12/2007 | De Boer et al. | 546/268.1 |
| 2001/0000519 A1 | 4/2001 | Bennett | 526/329 |
| 2001/0016634 A1 | 8/2001 | Ittel et al. | 526/172 |
| 2002/0013431 A1 | 1/2002 | Bennett | 526/90 |
| 2002/0016425 A1 | 2/2002 | De Boer et al. | 526/172 |
| 2002/0016521 A1 | 2/2002 | Culver et al. | 585/527 |
| 2002/0019575 A1 | 2/2002 | Schiffino | 585/520 |
| 2002/0028941 A1 | 3/2002 | De Boer et al. | 546/167 |
| 2002/0035031 A1 | 3/2002 | Berardi et al. | 502/171 |
| 2002/0128409 A1 | 9/2002 | De Boer et al. | 526/172 |
| 2003/0036615 A1 | 2/2003 | Brookhart, III et al. | 526/161 |
| 2003/0045658 A1 | 3/2003 | Wang et al. | 526/113 |
| 2003/0045752 A1 | 3/2003 | De Boer et al. | 562/545 |
| 2003/0050494 A1 | 3/2003 | Brookhart, III et al. | 556/138 |
| 2003/0119921 A1 | 6/2003 | De Boer et al. | 518/715 |
| 2003/0125195 A1 | 7/2003 | Britovsek et al. | 502/117 |
| 2003/0144514 A1 | 7/2003 | De Boer et al. | 546/12 |
| 2003/0195110 A1 | 10/2003 | Moody et al. | 502/150 |
| 2003/0225228 A1 | 12/2003 | Moody et al. | 526/172 |
| 2004/0116758 A1 | 6/2004 | De Boer et al. | 585/521 |
| 2005/0014983 A1 | 1/2005 | De Boer et al. | 585/511 |
| 2005/0159601 A1 | 7/2005 | De Boer et al. | 546/2 |
| 2008/0058485 A1 | 3/2008 | Wang et al. | 526/147 |

FOREIGN PATENT DOCUMENTS

| | | |
|---|---|---|
| EP | 0308728 | 3/1989 |
| EP | 0308728 A1 | 3/1989 |
| EP | 0927201 B1 | 7/1999 |
| EP | 1125928 | 8/2001 |
| EP | 1127987 | 8/2001 |
| JP | 4325504 | 11/1992 |
| SU | 418462 | 3/1974 |
| WO | 92/12162 | 7/1992 |
| WO | 96/27439 | 9/1996 |
| WO | 98/27124 | 6/1998 |
| WO | 99/02472 | 1/1999 |
| WO | 99/12981 | 3/1999 |
| WO | 99/50273 | 10/1999 |
| WO | 99/51550 | 10/1999 |
| WO | 99/62967 | 12/1999 |
| WO | 00/08034 | 2/2000 |
| WO | 00/15646 | 3/2000 |
| WO | 00/20427 | 4/2000 |
| WO | 00/24788 | 5/2000 |
| WO | 00/50470 | 8/2000 |
| WO | WO0123444 A1 | 4/2001 |
| WO | WO0123445 A1 | 4/2001 |
| WO | 01/36379 | 5/2001 |
| WO | 01/58874 | 8/2001 |
| WO | 02/00339 | 1/2002 |
| WO | 02/06192 | 1/2002 |
| WO | 02/12151 | 2/2002 |
| WO | 02/28805 | 4/2002 |
| WO | 03/000628 | 1/2003 |
| WO | 03/011876 | 2/2003 |

OTHER PUBLICATIONS

Gibson Vernon C et al: "The nature of the active species in bis(imino) pyridyl cobalt ethylene polymerisations catalysts" Chemical Communications Chemcom, Royal Society of Chemistry, GB, No. 21, 2001, pp. 2252-2253. XP002196345 ISSN 1359-7345.

Small et al: "Iron-Based Catalysts with Exceptionally High Activities and Selectivities for Oligormerization of Ethylene to Linear.alpha.-Olefins" Journal of the American Chemical Society, Washington, DC, US, vol. 120, No. 28 Jul. 22, 1998, pp. 7143-7144, XP002086898 ISSN:0002-7863.

Ittel S D et al: "late-metal catalysts for ethylene homo- and copolymerization" chemical reviews, american chemical society. Easton, US, vol. 100, No. 4, 2000, pp. 1169-1203, Xp00093140.

Britovsek G J P et al: "oligomerisation of ethylene by bis(imino)pyridyliron and -cobalt complexes" Chemistry—a European journal, VCH publishers, US vol. 6, No. 12, 2000, pp. 2221-2231, XP000942739, ISSN 0947-6539.

Britovsek et al: "Novel olefin polymerization catalysts based on iron and cobalt" Chemical communications—chemcom, royal society of chemistry, GB No. 7, 1998, pp. 849-850, XP002086893 ISSN 1359-7345.

D. Vogt, Oligomerisation of ethylene to higher alpah-olefins in Applied Homogeneous Catalysis with organometallic Compounds, Ed. B. Cornils, W.A. Herrmann, 2nd Edition, vol. 1, Ch. 2.3.1.1, p. 240-253, Wiley-VCH 2002.

International Preliminary Examination Report for PCT/EP03/10708 of Jan. 3, 2005.

Office Action of Nov. 29, 2004 in U.S. Appl. No. 10/208,535.

Amendment in response to office action of Nov. 29, 2004 in U.S. Appl. No. 10/208,535.

D. van Leusen and B. Hessen, Organometallics, 2001, 20, pp. 224-226.

Chemical Abstracts, vol. 134, Columbus, Ohio, US; Abstract No. 231149, Radecka-Paryzek, W. et. al., "Metal-Ion-Directed Synthesis of Homo- and Heteronuclear Dimetallic Schiff Base Podates," Pol. J. Chem. 2001, 75(1), pp. 35-42.

Olefin Polymerization with [{bis(imino)pyridyl}CO CI2]: Generation of the Active Species Involves CO, by T. Martijn Kooistra et al., Angewandte Chemie. International Edition, Wiley-VCH, Weinheim, DE, vol. 40, No. 24, Dec. 17, 2001, pp. 4719-4722.

D. Vogt, Oligomerisation of ethylene to higher a-olefins in Applied Homgeneous Catalysis with Organometallic Compounds Ed. B. Cornils, W.A. Herrmann vol. 1, Ch. 2.3.1.3, p. 245, VCH 1996.

Lions, Francis et al. "Tridentate Chelate Compounds. I" J. Am. Chem. Soc. (1957), vol. 79, 2733-38.

Figgins, Paul et al., "Complexes of Irong(II), Co(II), and Ni(II) with Biacetyl-bis-methylimine, 2-pyridinal-methylimine and 2,6-pyridindial-bis-methylimine," J. Am. Chem. Soc. (1960), vol. 82, 820-824.

Small, Am Chem Soc, vol. 32, No. 7, Jun. 4, 1999, pp. 2120-2130, XP000823810.

"Novel, Highly Active Iron and Cobalt Catalysts for Olefin Polymerization", by Alison M. A. Bennett, Chemtech, Jul. 1999, pp. 24-28.

"Polymerization of Propylene by a New Generation of Iron Catalysts: Mechanisms of Chain Initiation, Propagation, and Termination," by Brooke L. Small and Maurice Brookhart, Macromolecules, vol. 32, No. 7, 1999, pp. 2120-2130.

"1,1'-Diisocyanoferrocene and a Convenient Synthesis of Ferrocenylamine," by Daan van Leusen and Bart Hessen, Organometallics, 2001, pp. 224-226.

U.S. Appl. No. 09/964,714, filed Sep. 27, 2001, De Boer et al.
U.S. Appl. No. 10/208,535, filed Jul. 30, 2002, De Boer et al.
U.S. Appl. No. 10/739,715, filed Dec. 18, 2003, De Boer et al.
U.S. Appl. No. 10/320,213, filed Dec. 16, 2002, De Boer et al.
U.S. Appl. No. 11/080,170, filed Mar. 15, 2005, De Boer et al.

U.S. Appl. No. 10/883,600, filed Jul. 1, 2004, De Boer et al.
U.S. Appl. No. 10/668,592, filed Sep. 23, 2003, De Boer et al.
"Tridentate Cobalt Catalysts for Linear Dimerization and Isomerization of α-Olefins," by Brooke L. Small, *Organometallics* 2003, 22, pp. 3178-3183.
Leyong Wang et al., "Late transition metal complexes bearing 2,9-bis(imino)-1,10-phenanthrolinyl ligands: synthesis, characterization and their ethylene activity," *Journal of Organometallic Chemistry*, 658 (2002), pp. 62-70.
Yaofeng Chen et al., Fluoro-Substituted 2,6-Bis(imino)pyridyl Iron and Cobalt Complexes: High-Activity Ethylene Oligomerization Catalysts, *Organometallics* 2003, 22, pp. 1231-1236.

* cited by examiner

TRANSITION METAL COMPLEXES

FIELD OF THE INVENTION

The present invention relates to transition metal complexes based on certain bis-arylimine pyridine ligands and catalyst systems prepared therefrom, wherein the transition metal complexes and the catalyst systems prepared therefrom are highly soluble in non-polar media, and the use of such transition metal complexes for the dimerization and oligomerization of olefins.

BACKGROUND OF THE INVENTION

Several transition metal complexes based upon bis-imine pyridine ligands have been reported in the art, in particular for use in catalyst systems for the catalysis of ethylene and/or olefin (co-) polymerization and (co-) oligomerization reactions as well as for use in catalyst systems for the catalysis of alpha-olefin dimerization reactions.

In this regard a number of published patent applications describe catalyst systems for the polymerization or oligomerization of 1-olefins, in particular ethylene, which contain nitrogen-containing transition metal compounds. See, for example, the following patent applications which are incorporated herein by reference in their entirety: WO 92/12162, WO 96/27439, WO 99/12981, WO 00/50470, WO 98/27124, WO 99/02472, WO 99/50273, WO 99/51550, EP-A-1,127, 987, WO 02/12151, WO 02/06192, WO 99/12981, WO 00/24788, WO 00/08034, WO 00/15646, WO 00/20427, WO 01/58874 and WO 03/000628.

In particular, recently published Shell applications WO01/58874, WO02/00339, WO02/28805 and WO 03/011876, all of which are incorporated herein by reference in their entirety, disclose novel classes of catalysts based on bis-imine pyridine iron compounds which are highly active in the oligomerization of olefins, especially ethylene and which produce linear alpha olefins in the $C_6$-$C_{30}$ range with a Schulz-Flory distribution, said linear alpha olefins being of high purity.

In co-pending PCT Patent Application No. PCT/EP03/10708 (now published as WO 2004/037415), there is described a catalyst system for the oligomerization of ethylene to linear alpha olefins, wherein the catalyst system comprises:

a) one or more bis-arylimine pyridine iron or cobalt catalysts;

b) a first co-catalyst compound which is selected from aluminium alkyls, aluminoxanes, and mixtures thereof; and c) one or more additional co-catalyst compounds which comprises one or more compounds of the formula $ZnR'_2$ wherein each R', which may be the same or different, is selected from hydrogen, optionally substituted $C_1$-$C_{20}$ hydrocarbyl, phenyl, Cl, Br, I, SR", NR"$_2$, OH, OR", CN, NC wherein R", which within the same molecule may be the same or different, is $C_1$-$C_{20}$ hydrocarbyl.

Co-pending PCT Patent Application No. PCT/EP03/10708 (now published as WO 2004/037415) describes bis-arylimine pyridine ligands having the formula below:

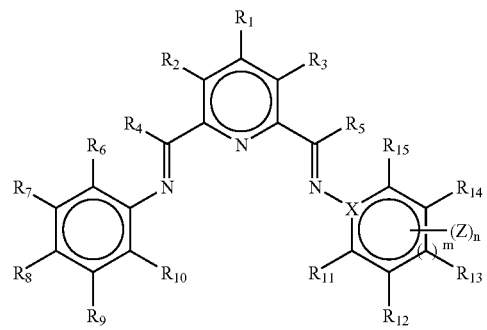

wherein X is carbon or nitrogen,
n is 0 or 1,
m is 0 or 1,
Z is a π-coordinated metal fragment,
$R_1$-$R_5$, $R_7$-$R_9$ and $R_{12}$-$R_{14}$ are each, independently, hydrogen, optionally substituted hydrocarbyl, an inert functional group, or any two of $R_1$-$R_3$, $R_7$-$R_9$ and $R_{12}$-$R_{14}$ vicinal to one another taken together may form a ring; $R_6$ is hydrogen, optionally substituted hydrocarbyl, an inert functional group, or taken together with $R_7$ or $R_4$ to form a ring; $R_{10}$ is hydrogen, optionally substituted hydrocarbyl, an inert functional group, or taken together with $R_9$ or $R_4$ to form a ring; $R_{11}$ is hydrogen, optionally substituted hydrocarbyl, an inert functional group, or taken together with $R_5$ or $R_{12}$ to form a ring; and $R_{15}$ is hydrogen, optionally substituted hydrocarbyl, an inert functional group, or taken together with $R_5$ or $R_{14}$ to form a ring.

Disclosed within the examples of co-pending PCT Patent Application No. PCT/EP03/10708 (now published as WO 2004/037415) is the 2-[1-(2,4,6-trimethylphenylimino) ethyl]-6-[1-(4-eicosanoxy-3,5-diphenylphenylimino)ethyl] pyridine iron[II] chloride complex, and catalyst systems consisting of 2-[1-(2,4,6-trimethylphenylimino)ethyl]-6-[1-(4-eicosanoxy-3,5-diphenylphenylimino)ethyl]pyridine iron [II] chloride with MAO and 2-[1-(2,4,6-trimethylphenylimino)ethyl]-6-[1-(4-eicosanoxy-3,5-diphenylphenylimino)ethyl]pyridine iron[II] chloride with methylaluminoxane (MAO) and $Et_2Zn$ co-catalysts in a toluene solution.

U.S. Pat. No. 6,291,733, describes a method of dimerizing alpha-olefins to mostly linear internal olefin dimers using a catalyst composition comprising a bis-arylimine pyridine iron complex and an alkylaluminoxane co-catalyst composition in molar excess. The reaction of this process proceeds rapidly, even at ambient temperatures, and yields a dimerization product rich in linear internal olefin dimers.

The use of a bis-arylimine pyridine cobalt complex and a modified methylaluminoxane (MMAO) co-catalyst in the dimerization of alpha-olefins is described in the article "Tridentate Cobalt Catalysts for Linear Dimerization and Isomerization of α-Olefins" by Brooke L. Small in Organometallics 2003, 22, 3178-3183. The use of a molar excess of the alkylaluminoxane co-catalyst in this reference makes this process commercially less favourable.

Although catalysts based on bis-arylimine pyridine complexes are useful catalyst precursors in polymerization, oligomerization and dimerization processes, they suffer from the disadvantage that they have low solubility in non-polar media, especially at ambient temperatures. The low solubility of bis-arylimine pyridine complexes in non-polar media such as benzene, toluene and paraffin solvents, especially at ambient temperatures, has several problems attached to it, including difficulty in accurate dosing of the catalyst system into reactors, especially under continuous operation, and damage to the reactor equipment, especially pumps and seals which can be caused by the abrasive action of suspended, non-soluble catalyst particles.

Therefore, there is a need for bis-arylimine pyridine complexes and catalyst systems comprising these complexes which can be used with ease in a continuous process, e.g. continuous polymerization, oligomerization or dimerization process. In particular, there is a need for bis-arylimine pyridine complexes and catalyst systems containing such complexes which are highly soluble in non-polar media, without having a deleterious effect on the catalytic activity displayed by the bis-arylimine pyridine catalyst compositions known in the art.

The present invention provides a transition metal complex based on certain bis-arylimine pyridine ligands and a catalyst system thereof which are highly soluble in non-polar media and display good catalytic activity for continuous polymerization, oligomerization and dimerization processes.

SUMMARY OF THE INVENTION

In one aspect of the present invention there is provided a transition metal complex which is a bis-arylimine pyridine $MX_n$ complex, comprising a bis-arylimine pyridine ligand having the formula (I) below:

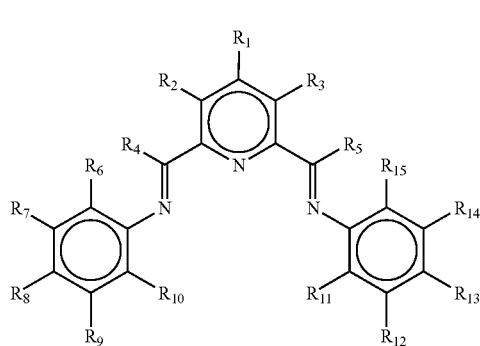

(I)

wherein $R_1$-$R_5$, $R_7$-$R_9$, $R_{12}$ and $R_{14}$ are each, independently, hydrogen, optionally substituted hydrocarbyl, an inert functional group, or any two of $R_1$-$R_3$ and $R_7$-$R_9$ vicinal to one another taken together may form a ring, and $R_6$ is hydrogen, optionally substituted hydrocarbyl, an inert functional group, or taken together with $R_7$ or $R_4$ to form a ring, $R_{10}$ is hydrogen, optionally substituted hydrocarbyl, an inert functional group, or taken together with $R_9$ or $R_4$ to form a ring, $R_{11}$ is hydrogen, optionally substituted hydrocarbyl, an inert functional group, or taken together with $R_{12}$ or $R_5$ to form a ring, $R_{15}$ is hydrogen, optionally substituted hydrocarbyl, an inert functional group, or taken together with $R_{14}$ or $R_5$ to form a ring, provided that $R_{13}$ and at least one of $R_{12}$ and $R_{14}$ are independently selected from optionally substituted $C_1$-$C_{30}$ alkyl, optionally substituted $C_4$-$C_{30}$ alkyloxy, halogen and optionally substituted $C_5$-$C_{20}$ aryl, or $R_{13}$ taken together with $R_{12}$ or $R_{14}$ form a ring, or $R_{12}$ taken together with $R_{11}$ form a ring and $R_{14}$ taken together with $R_{15}$ form a ring (preferably wherein $R_{13}$ and at least one of $R_{12}$ and $R_{14}$ are independently selected from optionally substituted $C_1$-$C_{30}$ alkyl, optionally substituted $C_4$-$C_{30}$ alkyloxy and optionally substituted $C_5$-$C_{20}$ aryl), and provided that at least one of $R_{12}$, $R_{13}$ and $R_{14}$ is optionally substituted $C_4$-$C_{30}$ alkyloxy;

M is a transition metal atom selected from Ti, V, Cr, Mn, Ni, Pd, Rh, Ru, Mo, Nb, Zr, Hf, Ta, W, Re, Os, Ir or Pt; preferably Ti, V, Cr, Mn, Ni, Pd or Pt; more preferably V, Cr, Mn, Ni or Pd; especially Cr;

n matches the formal oxidation state of transition metal atom M; and

X is halide, optionally substituted hydrocarbyl, alkoxide, amide, or hydride.

In another aspect of the present invention, there is provided a transition metal complex which is a bis-arylimine pyridine $MX_n$ complex, comprising a bis-arylimine pyridine ligand having the formula (I) above, wherin $R_{1-15}$ and X are as defined above in relation to formula I and M is a transition metal atom, especially one selected from Fe and Co, wherein the transition metal complex is not 2-[1-(2,4,6-trimethylphenylimino)ethyl]-6-[1-(4-eicosanoxy-3,5-diphenylphenylimino)ethyl]pyridine iron (II) chloride complex.

In another aspect of the present invention there is provided a transition metal complex which is a [bis-arylimine pyridine $MX_p^+$] [$NC^-$]$_q$ complex, comprising a bis-arylimine pyridine ligand having the formula (I) below:

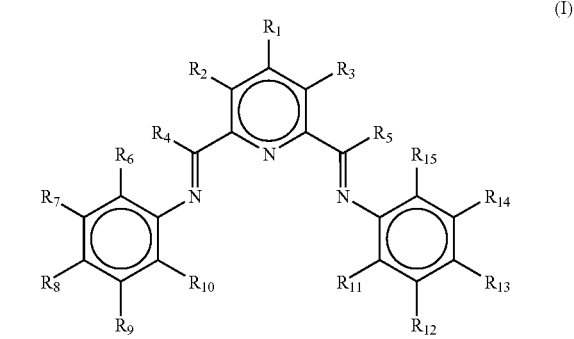

(I)

wherein $R_1$-$R_5$, $R_7$-$R_9$, $R_{12}$ and $R_{14}$ are each, independently, hydrogen, optionally substituted hydrocarbyl, an inert functional group, or any two of $R_1$-$R_3$ and $R_7$-$R_9$ vicinal to one another taken together may form a ring, and $R_6$ is hydrogen, optionally substituted hydrocarbyl, an inert functional group, or taken together with $R_7$ or $R_4$ to form a ring, $R_{10}$ is hydrogen, optionally substituted hydrocarbyl, an inert functional group, or taken together with $R_9$ or $R_4$ to form a ring, $R_{11}$ is hydrogen, optionally substituted hydrocarbyl, an inert functional group, or taken together with $R_{12}$ or $R_5$ to form a ring, $R_{15}$ is hydrogen, optionally substituted hydrocarbyl, an inert functional group, or taken together with $R_{14}$ or $R_5$ to form a ring, provided that $R_{13}$ and at least one of $R_{12}$ and $R_{14}$ are independently selected from optionally substituted $C_1$-$C_{30}$ alkyl, optionally substituted $C_4$-$C_{30}$ alkyloxy, halogen and optionally substituted $C_5$-$C_{20}$ aryl, or $R_{13}$ taken together with $R_{12}$ or $R_{14}$ form a ring, or $R_{12}$ taken together with $R_{11}$ form a ring and $R_{14}$ taken together with $R_{15}$ form a ring (preferably $R_{13}$ and at least one of $R_{12}$ and $R_{14}$ are independently selected from optionally substituted $C_1$-$C_{30}$ alkyl, optionally substituted $C_4$-$C_{30}$ alkyloxy and optionally substituted $C_5$-$C_{20}$ aryl), and provided that at least one of $R_{12}$, $R_{13}$ and $R_{14}$ is optionally substituted $C_4$-$C_{30}$ alkyloxy;

X is halide, optionally substituted hydrocarbyl, alkoxide, amide, or hydride;

M is a transition metal atom selected from Ti, V, Cr, Mn, Ni, Pd, Rh, Ru, Mo, Nb, Zr, Hf, Ta, W, Re, Os, Ir or Pt; preferably Ti, V, Cr, Mn, Ni, Pd or Pt; more preferably V, Cr, Mn, Ni or Pd; especially Cr; or M is a transition metal atom, particularly Fe or Co;

NC⁻ is a non-coordinating anion; and p+q matches the formal oxidation state of transition metal atom M.

In another aspect of the invention, there is provided a transition metal complex, which is (a) a bis-arylimine pyridine MX$_n$ complex comprising a bis-arylimine pyridine ligand having the formula (I) above wherein R$_{1-15}$, X and n are as defined and described herein in relation to formula I and M is a transition metal atom, e.g. as described above but preferably Fe, Co or Cr or (b), a [bis-arylamine pyridine MX$_p^+$] [NC⁻]$_q$ complex comprising a bis-arylimine pyridine ligand having the formula (I) above wherein R$_{1-15}$, X, p, [NC] and q are as defined and described herein in relation to formula (I) and M is a transition metal atom, e.g. as described above but preferably selected from Fe, Co and Cr, provided that in the ligand of formula (I) in said transition metal complex R$_8$ and at least one of R$_7$ and R$_9$ are independently selected from optionally substituted C$_1$-C$_{30}$ alkyl, optionally substituted C$_4$-C$_{30}$ alkyloxy, halogen and optionally substituted C$_5$-C$_{20}$ aryl, or R$_8$ taken together with R$_7$ or R$_9$ form a ring, or R$_7$ taken together with R$_6$ form a ring and R$_9$ taken together with R$_{10}$ form a ring (preferably wherein R$_8$ and at least one of R$_7$ and R$_9$ are independently selected from optionally substituted C$_1$-C$_{30}$ alkyl, optionally substituted C$_4$-C$_{30}$ alkyloxy and optionally substituted C$_5$-C$_{20}$ aryl), and provided that at least one of R$_7$, R$_8$ and R$_9$ is optionally substituted C$_4$-C$_{30}$ alkyloxy. A ligand of formula I having such a definition of R$_7$, R$_8$, R$_9$ as given in this paragraph is also described herein as one of formula II.

In another aspect of the present invention there is provided a catalyst system comprising (a) one or more of the transition metal complexes which is a bis-arylimine pyridine MX$_n$ complex where the bis-arylimine pyridine is of formula I above in which R$_{1-15}$, X, n are as defined and described herein in relation to formula I and M is a transition metal atom e.g. as described herein in relation to formula I including Fe or Co, or is a [bis-arylimine pyridine MX$_p^+$] m[NC⁻]$_q$ complex wherein the bis-arylimine pyridine is of formula I above in which R$_{1-15}$, X, p, q [NC] are as defined and described herein in relation to formula I and M is a transition metal atom, e.g. as described herein in relation to formula I include Fe or Co, and mixtures thereof and (b)(i) in the case when a bis-arylimine pyridine MX$_n$ complex is present, (1) a co-catalyst compound capable of abstracting an anion and transferring an optionally substituted hydrocarbyl or hydride group to the metal atom, or (2) a co-catalyst compound capable of abstracting an anion and a co-catalyst compound capable of transferring an optionally substituted hydrocarbyl or hydride group to the transition metal atom; and/or (b)(ii) in the case where a [bis-arylimine pyridine MX$_p^+$] [NC⁻]$_q$ complex is present, a co-catalyst compound capable of transferring an optionally substituted hydrocarbyl or hydride group to the transition metal atom;

with the proviso that when the transition metal atom is Fe or Co the catalyst system does not comprise one or more compounds of the formula ZnR'$_2$ wherein each R', which may be the same or different, is selected from hydrogen, optionally substituted C$_1$-C$_{20}$ hydrocarbyl, phenyl, Cl, Br, I, SR", NR"2, OH, OR", CN, isocyanide wherein R", which within the same molecule may be the same or different, is C$_1$-C$_{20}$ hydrocarbyl, and the catalyst system is not 2-[1-(2,4,6-trimethylphenylimino)ethyl]-6-[1-(4-eicosanoxy-3,5-diphenylphenylimino)ethyl]pyridine iron[II] chloride complex with MAO.

or with the proviso that when the transition metal is Fe the catalyst system is not 2-[1-(2,4,6-trimethylphenylimino)ethyl]-6-[1-(4-eicosanoxy-3,5-diphenylphenylimino)ethyl] pyridine iron (II) chloride with MAO or 2-[1-(2,4,6-trimethylphenylimino)ethyl]-6-[1-(4-eicosanoxy-3,5-diphenylphenylimino)ethyl]pyridine iron (II) chloride with MAO and ZnEt$_2$.

In another aspect, there is provided a modified catalyst system of the invention comprising component (b) immediately above and component (a) which comprises one or more of the transition metal complexes which may be a bis-arylimine pyridine MX$_n$ or [MX$_p^+$] [NC⁻]$_q$ complex, where X, p, NC and q are as defined and described herein in relation to formula I and M is a transition metal atom e.g. as described herein in relation to formula I including Fe or Co, and R$_{1-15}$ are as defined and described with respect to formula I, provided that R$_7$, R$_8$ and R$_9$ are as defined above in relation to ligands of formula II.

In another aspect of the present invention, there is provided a dimerization or co-oligomerisation process comprising contacting an olefin feed which is an alpha-olefin comprising at least 3 carbon atoms or a mixture thereof with ethylene, with a catalyst composition comprising:

(a) one or more transition metal complexes selected from:
(i) a bis-arylimine pyridine MX$_n$ complexes, comprising a bis-arylimine pyridine ligand having the formula (I) below:

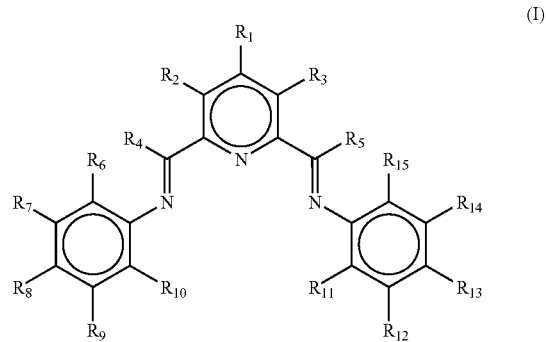

(I)

wherein R$_1$-R$_5$, R$_7$-R$_9$, R$_{12}$ and R$_{14}$ are each, independently, hydrogen, optionally substituted hydrocarbyl, an inert functional group, or any two of R$_1$-R$_3$ and R$_7$-R$_9$ vicinal to one another taken together may form a ring, and R$_6$ is hydrogen, optionally substituted hydrocarbyl, an inert functional group, or taken together with R$_7$ or R$_4$ to form a ring, R$_{10}$ is hydrogen, optionally substituted hydrocarbyl, an inert functional group, or taken together with R$_9$ or R$_4$ to form a ring, R$_{11}$ is hydrogen, optionally substituted hydrocarbyl, an inert functional group, or taken together with R$_{12}$ or R$_5$ to form a ring, R$_{15}$ is hydrogen, optionally substituted hydrocarbyl, an inert functional group, or taken together with R$_{14}$ or R$_5$ to form a ring, provided that R$_{13}$ and at least one of R$_{12}$ and R$_{14}$ are independently selected from optionally substituted C$_1$-C$_{30}$ alkyl, optionally substituted C$_4$-C$_{30}$ alkyloxy, halogen and optionally substituted C$_5$-C$_{20}$ aryl, or R$_{13}$ taken together with R$_{12}$ or R$_{14}$ form a ring, or R$_{12}$ taken together with R$_{11}$ form a ring and R$_{14}$ taken together with R$_{15}$ form a ring (preferably wherein R$_{13}$ and at least one of R$_{12}$ and R$_{14}$ are independently selected from optionally substituted C$_1$-C$_{30}$ alkyl, optionally substituted C$_4$-C$_{30}$ alkyloxy and optionally substituted $C_5$-$C_{20}$ aryl), and provided that at least one of $R_{12}$, $R_{13}$ and $R_{14}$ is optionally substituted $C_4$-$C_{30}$ alkyloxy;

M is a transition metal atom; preferably a Group 4 to Group 10 transition metal; preferably Ti, V, Cr, Mn, Fe, Co, Ni, Pd or Pt; more preferably V, Cr, Mn, Fe, Co, Ni or Pd; especially Fe, Co or Cr;

n matches the formal oxidation state of transition metal atom M; and

X is halide, optionally substituted hydrocarbyl, alkoxide, amide, or hydride; and (ii) a [bis-arylimine pyridine $MX_p{}^+$] $[NC^-]_q$ complex, comprising a bis-arylimine pyridine ligand having the formula (I) below:

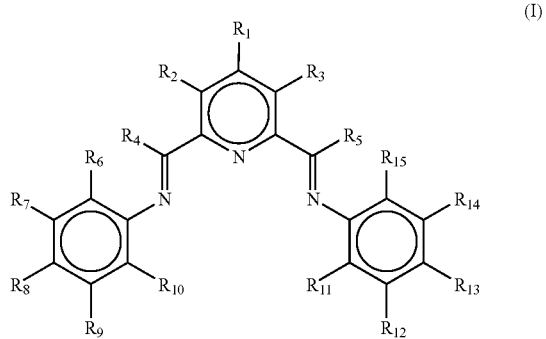

wherein $R_1$-$R_5$, $R_7$-$R_9$, $R_{12}$ and $R_{14}$ are each, independently, hydrogen, optionally substituted hydrocarbyl, an inert functional group, or any two of $R_1$-$R_3$ and $R_7$-$R_9$ vicinal to one another taken together may form a ring, and $R_6$ is hydrogen, optionally substituted hydrocarbyl, an inert functional group, or taken together with $R_7$ or $R_4$ to form a ring, $R_{10}$ is hydrogen, optionally substituted hydrocarbyl, an inert functional group, or taken together with $R_9$ or $R_4$ to form a ring, $R_{11}$ is hydrogen, optionally substituted hydrocarbyl, an inert functional group, or taken together with $R_{12}$ or $R_5$ to form a ring, $R_{15}$ is hydrogen, optionally substituted hydrocarbyl, an inert functional group, or taken together with $R_{14}$ or $R_5$ to form a ring, provided that $R_{13}$ and at least one of $R_{12}$ and $R_{14}$ are independently selected from optionally substituted $C_1$-$C_{30}$ alkyl, optionally substituted $C_4$-$C_{30}$ alkyloxy, halogen and optionally substituted $C_5$-$C_{20}$ aryl, or $R_{13}$ taken together with $R_{12}$ or $R_{14}$ form a ring, or $R_{12}$ taken together with $R_{11}$ form a ring and $R_{14}$ taken together with $R_{15}$ form a ring (preferably $R_{13}$ and at least one of $R_{12}$ and $R_{14}$ are independently selected from optionally substituted $C_1$-$C_{30}$ alkyl, optionally substituted $C_4$-$C_{30}$ alkyloxy and optionally substituted $C_5$-$C_{20}$ aryl), and provided that at least one of $R_{12}$, $R_{13}$ and $R_{14}$ is optionally substituted $C_4$-$C_{30}$ alkyloxy;

X is halide, optionally substituted hydrocarbyl, alkoxide, amide, or hydride;

M is a transition metal atom; preferably a Group 4 to Group 10 transition metal; preferably Ti, V, Cr, Mn, Fe, Co, Ni, Pd or Pt; more preferably V, Cr, Mn, Fe, Co, Ni or Pd; especially Fe, Co or Cr;

$NC^-$ is a non-coordinating anion; and p+q matches the formal oxidation state of transition metal atom M; and mixtures thereof; and (b)(i) in the case when a bis-arylimine pyridine $MX_n$ complex is present, (1) a co-catalyst compound capable of abstracting an anion and transferring an optionally substituted hydrocarbyl or hydride group to the metal atom, or (2) a co-catalyst compound capable of abstracting an anion and a co-catalyst compound capable of transferring an optionally substituted hydrocarbyl or hydride group to the transition metal atom; and/or (b)(ii) in the case where a [bis-arylimine pyridine $MX_p{}^+$] $[NC^-]_q$ complex is present, a co-catalyst compound capable of transferring an optionally substituted hydrocarbyl or hydride group to the transition metal atom.

When the feed olefin is an alpha olefin of at least 3 carbon atoms, the process is a dimerization, but when the feed olefin is a mixture thereof with ethylene it is a co-oligomerization process.

In another aspect of the present invention there is provided an oligomerization process comprising contacting an olefin feed which is ethylene with a catalyst system (also called herein a catalyst) composition comprising (a) one or more transition metal complexes which is a bis-arylimine pyridine $MX_n$ complex where the bis-arylimine pyridine of formula I above in which $R_{1-15}$, X, n are as defined and described herein in relation to formula I and M is a transition metal atom e.g. as described herein in relation to formula I including Fe or Co, or is a [bis-arylimine pyridine $MX_p$] $[NC^-]_q$ complex wherein the bis arylamine pyridine is of formula I above in which $R_{1-15}$, X, p, q, [NC] are as defined and described herein in relation to formula I and M is a transition metal atom, eg as described herein in relation to formula I (including Fe or Co), in particular in relation to the dimerization process, and mixtures thereof and (b)(i) in the case when a bis-arylimine pyridine $MX_n$ complex is present, (1) a co-catalyst compound capable of abstracting an anion and transferring an optionally substituted hydrocarbyl or hydride group to the metal atom, or (2) a co-catalyst compound capable of abstracting an anion and a co-catalyst compound capable of transferring an optionally substituted hydrocarbyl or hydride group to the transition metal atom; and/or (b)(ii) in the case where a [bis-arylimine pyridine $MX_p{}^+$] $[NC^-]_q$ complex is present, a co-catalyst compound capable of transferring an optionally substituted hydrocarbyl or hydride group to the transition metal atom with the proviso that when the transition metal atom is Fe or Co the catalyst system does not comprise one or more compounds of the formula $ZnR'_2$ wherein each R', which may be the same or different, is selected from hydrogen, optionally substituted $C_1$-$C_{20}$ hydrocarbyl, phenyl, Cl, Br, I, SR", NR"$_2$, OH, OR", CN, NC wherein R", which within the same molecule may the same or different, is $C_1$-$C_{20}$ hydrocarbyl, and the catalyst system is not 2-[1-(2,4,6-trimethylphenylimino) ethyl]-6-[1-(4-eicosanoxy-3,5-diphenylphenylimino)ethyl] pyridine iron[II] chloride complex with MAO, or with the proviso that when the transition metal is Fe the catalyst system is not 2-[1-(2,4,6-trimethylphenylimino) ethyl]-6-[1-(4-eicosanoxy-3,5-diphenylphenylimino)ethyl] pyridine iron (II) chloride with MAO or 2-[1-(2,4,6-trimethylphenylimino)ethyl]-6-[1-(4-eicosanoxy-3,5-diphenylphenylimino)ethyl]pyridine iron (II) chloride with MAO and $ZnEt_2$.

In a modification of this aspect of the present invention there is provided an oligomerization process comprising contacting an olefin feed which is ethylene with the modified catalyst system of the invention.

The transition metal complexes and catalyst systems of the present invention have excellent solubility in non-polar media and can be used to catalyze a wide variety of oligomerization, polymerization and dimerization reactions.

In another aspect of the present invention, there is provided a solution in non-polar media, in particular a chemically inert non-polar solvent, especially an aromatic hydrocarbon solvent, of at least 5 or 10 mg ml$^{-1}$ of a transition metal complex which is a bis-arylimine pyridine $MX_n$ or $[MX_p^+][NC^-]_q$ complex each comprising a bis-arylimine pyridine complex of formula I as defined and described above wherein each of $R_{1-15}$, X, n, p, NC and q are as defined and described herein, and M is a transition metal, such as one from any of Groups 4 to 10, in particular one selected from Ti, V, Cr, Mn, Fe, Co, Ni, Pd, Rh, Ru, Mo, Nb, Zr, Hf, Ta, W, Re, Os, Ir or Pt, preferably Fe, Co or Cr and especially Co or Fe. A preferred solution is in toluene of at least 10 mg ml$^{-1}$ especially at least 50 mg ml$^{-1}$ of the transition metal complex wherein the metal M is iron or cobalt, in particular 2-[1-(2,4,6-trimethylphenylimino) ethyl]-6-[1-4-eicosanoxy-3,5-diphenylphenylimino)ethyl] pyridine iron (II) chloride complex. In a further solution aspect of the present invention there is provided a solution in non-polar media in particular chemically inert non-polar solvents especially an aromatic hydrocarbon solvent, of at least 5 or 10 mg ml$^{-1}$ of a catalyst system comprising (a) said transition metal complex and component (b) as defined above. The catalyst system solution can be made by mixing solutions of the complex (a) and component (b) and is optionally in the presence or absence of the reactant composition to be dimerized or (co)oligomerized. The same complex is preferred in the catalyst solution as in the above complex solution of the present invention.

In another aspect of the present invention, the dimerization, oligomerization or co-oligomerization processes of the invention are performed with the catalyst complex, composition or system being in a solution of the present invention, especially in one or more of an aromatic hydrocarbon, such as benzene, toluene or xylene, and an alkene such as 1-hexene, cis/trans 2-hexene or 1-octene.

There is also provided in this invention a bis-arylimine pyridine ligand having the formula (I) below:

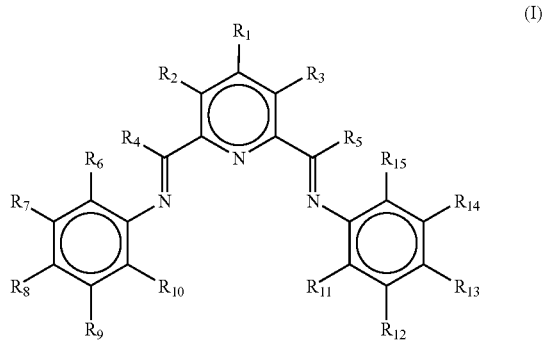

wherein $R_1$-$R_5$, $R_7$-$R_9$, $R_{12}$ and $R_{14}$ are each, independently, hydrogen, optionally substituted hydrocarbyl, an inert functional group, or any two of $R_1$-$R_3$ and $R_7$-$R_9$ vicinal to one another taken together may form a ring, and $R_6$ is hydrogen, optionally substituted hydrocarbyl, an inert functional group, or taken together with $R_7$ or $R_4$ to form a ring, $R_{10}$ is hydrogen, optionally substituted hydrocarbyl, an inert functional group, or taken together with $R_9$ or $R_4$ to form a ring, $R_{11}$ is hydrogen, optionally substituted hydrocarbyl, an inert functional group, or taken together with $R_{12}$ or $R_5$ to form a ring, $R_{15}$ is hydrogen, optionally substituted hydrocarbyl, an inert functional group, or taken together with $R_{14}$ or $R_5$ to form a ring, provided that $R_{13}$ and at least one of $R_{12}$ and $R_{14}$ are independently selected from optionally substituted $C_1$-$C_{30}$ alkyl, optionally substituted $C_4$-$C_{30}$ alkyloxy, halogen and optionally substituted $C_5$-$C_{20}$ aryl, or $R_{13}$ taken together with $R_{12}$ or $R_{14}$ form a ring, or $R_{12}$ taken together with $R_{11}$ form a ring and $R_{14}$ taken together with $R_{15}$ form a ring (preferably wherein $R_{13}$ and at least one of $R_{12}$ and $R_{14}$ are independently selected from optionally substituted $C_1$-$C_{30}$ alkyl, optionally substituted $C_4$-$C_{30}$ alkyloxy and optionally substituted $C_5$-$C_{20}$ aryl), and provided that at least one of $R_{12}$, $R_{13}$ and $R_{14}$ is optionally substituted $C_4$-$C_{30}$ alkyloxy;

wherein the bis-arylimine pyridine ligand is not 2-[1-(2,4,6-trimethylphenylimino)ethyl]-6-[1-(4-eicosanoxy-3,5-diphenylphenylimino)ethyl]pyridine. Preferably the ligands are of formula II as defined and described above.

DETAILED DESCRIPTION OF THE INVENTION

The present invention relates to transition metal complexes which comprise a bis-arylimine pyridine ligand having the formula (I) above wherein $R_{1-15}$, are as defined and described with reference to formula I.

In one class of complexes $R_{12}$, $R_{13}$ and $R_{14}$ are all independently selected from optionally substituted $C_1$-$C_{30}$ alkyl, optionally substituted $C_4$-$C_{30}$ alkyloxy, and optionally substituted $C_5$-$C_{20}$ aryl, with the proviso that at least one of $R_{12}$, $R_{13}$ and $R_{14}$ is optionally substituted $C_4$-$C_{30}$ alkyloxy.

In a preferred embodiment of the invention, $R_{13}$ and at least one of $R_{12}$ and $R_{14}$ are independently selected from optionally substituted $C_1$-$C_{30}$ (preferably $C_{3-25}$) alkyl, optionally substituted $C_4$-$C_{30}$ alkyloxy and optionally substituted $C_5$-$C_{20}$ (preferably $C_{3-25}$) aryl with the proviso that at least one of $R_{12}$, $R_{13}$ and $R_{14}$ is optionally substituted $C_4$-$C_{30}$ alkyloxy.

In one class of bis-arylimine pyridine transition metal complexes, the bis-arylimine pyridine ligand having formula (I) above, is such that $R_8$ and at least one of $R_7$ and $R_9$ are independently selected from optionally substituted $C_1$-$C_{30}$ alkyl, optionally substituted $C_4$-$C_{30}$ alkyloxy, halogen and optionally substituted $C_5$-$C_{20}$ aryl, or $R_8$ taken together with $R_7$ or $R_9$ form a ring, or $R_7$ taken together with $R_6$ form a ring and $R_9$ taken together with $R_{10}$ form a ring with the proviso that at least one of $R_7$, $R_8$ and $R_9$ is optionally substituted $C_4$-$C_{30}$ alkyloxy. Preferably $R_8$ and at least one of $R_7$ and $R_9$ are independently selected from optionally substituted $C_4$-$C_{30}$ alkyl, optionally substituted $C_4$-$C_{30}$ alkyloxy and optionally substituted $C_5$-$C_{20}$ aryl or are independently selected from optionally substituted $C_{3-25}$ alkyl, optionally substituted $C_4$-$C_{30}$ alkyloxy and optionally substituted $C_5$-$C_6$ aryl with the proviso that at least one of $R_7$, $R_8$ and $R_9$ is optionally substituted $C_4$-$C_{30}$ alkyloxy.

In another class of the complexes the ligand of formula I has $R_7$, $R_8$ and $R_9$ all independently selected from optionally substituted $C_1$-$C_{30}$ alkyl, optionally substituted $C_4$-$C_{30}$ alkyloxy and optionally substituted $C_5$-$C_{20}$ aryl with the proviso that at least one of $R_7$, $R_8$ and $R_9$ is optionally substituted $C_4$-$C_{30}$ alkyloxy.

It will be immediately apparent to the person skilled in the art, that when $R_8$ and at least one of $R_7$ and $R_9$ are independently selected from optionally substituted $C_4$-$C_{30}$ alkyl, optionally substituted $C_4$-$C_{30}$ alkyloxy and optionally substituted $C_5$-$C_{20}$ aryl with the proviso that at least one of $R_7$, $R_8$ and $R_9$ is optionally substituted $C_4$-$C_{30}$ alkyloxy, it is not possible for $R_8$ to be independently, hydrogen, optionally substituted hydrocarbyl, an inert functional group, or any two of $R_7$-$R_9$ vicinal to one another taken together to form a ring.

One type of transition metal complex herein is a bis-arylimine pyridine $MX_n$ complex comprising a bis-arylimine pyridine ligand having the formula (I) defined herein, and wherein:

M is a transition metal atom;

n matches the formal oxidation state of transition metal atom M; preferably n is 1, 2 or 3;

X is halide, optionally substituted hydrocarbyl, alkoxide, amide, or hydride; preferably halide or optionally substituted hydrocarbyl; more preferably halide; especially chlorine.

The bis-arylimine pyridine $MX_n$ complex disclosed herein can be reacted with a non-coordinating anion generating species to form a cationic complex, [bis-arylimine pyridine $MX_p^+$] $[NC^-]_q$ complex comprising a bis-arylimine pyridine ligand having the formula (I) defined herein, and wherein:

$NC^-$ is a non-coordinating anion; and p+q is 2 or 3, matching the formal oxidation state of transition metal atom M; preferably p+q is 2 or 3.

Like the bis-arylimine pyridine $MX_n$ complex, the cationic complex formed by the reaction of the bis-arylimine pyridine $MX_n$ complex with a non-coordinating anion generating species is advantageously highly soluble in non-polar media, and chemically inert non-polar solvents such as benzene and toluene. Furthermore, when the cationic complex of the present invention is used in a process of the invention of dimerization, co-oligomerization or oligomerization, a lower quantity of the compound (b) capable of transferring an optionally substituted hydrocarbyl or hydride group to the transition metal atom is required.

By the term "non-coordinating anion" is meant an anion which does not substantially coordinate to the metal atom M. Non-coordinating anions ($NC^-$) that may be suitably employed include bulky anions such as tetrakis [3,5-bis(trifluoromethyl)phenyl]borate ($BArF^-$), $(C_6F_5)_4B^-$, and anions of alkylaluminium compounds including $R_3AlX'^-$, $R_2AlClX'^-$, $RAlCl_2X'^-$, and "$RAlOX'^-$", wherein R is hydrogen, optionally substituted hydrocarbyl or an inert functional group, and X' is halide, alkoxide or oxygen. A preferred non-coordinating anion for use herein is tetrakis [3,5-bis(trifluoromethyl)phenyl]borate ($BArF^-$).

The term "Hydrocarbyl group" in relation to the $R_1$ to $R_{15}$ groups of formula (I) above means a group containing only carbon and hydrogen atoms. Unless otherwise stated, the number of carbon atoms is preferably in the range from 1 to 30, especially from 1 to 6. Unless otherwise stated, the hydrocarbyl group may be saturated or unsaturated, aliphatic, cycloaliphatic or cycloaromatic (e.g. phenyl), but is preferably aliphatic. Suitable hydrocarbyl groups include primary, secondary and tertiary carbon atom groups such as those described below.

The phrase "optionally substituted hydrocarbyl" in relation to the $R_1$ to $R_{15}$ groups of formula (I) above is used to describe hydrocarbyl groups which may optionally contain one or more "inert" heteroatom-containing functional groups. By "inert" it is meant that the functional groups do not interfere to any substantial degree with the catalytic process in which the transition metal complex may be employed. Non-limiting examples of such inert groups are halides, such as fluoride and chloride, silanes, stannanes, ethers, alkoxides and amines with adequate steric shielding, all well-known to those skilled in the art. Some examples of such groups include methoxy, trimethylsiloxy and eicosanoxy. Said optionally substituted hydrocarbyl may include primary, secondary and tertiary carbon atom groups of the nature described below.

The term "inert functional group" in relation to the $R_1$ to $R_{15}$ groups of formula (I) above means a group other than optionally substituted hydrocarbyl which is inert under the reaction conditions for any reaction or process in which the transition metal complex may be employed. By "inert" it is meant that the functional group does not interfere to any substantial degree with the catalytic process in which the transition metal complex may be employed. Examples of inert functional groups suitable for use herein include halides, ethers, and amines such as tertiary amines, preferably the inert functional group is a halide, especially fluorine and chlorine.

The term "Primary carbon atom group" as used herein means a —$CH_2$—R group wherein R is selected from hydrogen, an optionally substituted hydrocarbyl, or an inert functional group. Examples of suitable primary carbon atom groups include, but are not limited to, —$CH_3$, —$C_2H_5$, —$CH_2Cl$, —$CH_2OCH_3$, —$CH_2N(C_2H_5)_2$ and —$CH_2Ph$. Unless otherwise stated, preferred primary carbon atom groups for use herein are those wherein R is selected from hydrogen or a $C_1$-$C_6$ unsubstituted hydrocarbyl, preferably wherein R is hydrogen or a $C_1$-$C_3$ alkyl.

The term "Secondary carbon atom group" as used herein means a —$CH(R)_2$ group wherein each R is independently selected from an optionally substituted hydrocarbyl or an inert functional group. Alternatively, the two R groups may together represent a double bond moiety, e.g. =$CH_2$, or a cycloalkyl group. Examples of secondary carbon atom groups include, but are not limited to, —$CH(CH_3)_2$, —$CHCl_2$, —$CHPh_2$, —$CH$=$CH_2$ and cyclohexyl. Unless otherwise stated, preferred secondary carbon atom groups for use herein are those in which R is a $C_1$-$C_6$ unsubstituted hydrocarbyl, preferably a $C_1$-$C_3$ alkyl.

The term "Tertiary carbon atom group" as used herein means a —$C(R)_3$ group wherein each R is independently selected from an optionally substituted hydrocarbyl or an inert functional group. Alternatively, the three R groups may together represent a triple bond moiety, e.g. —C≡CPh, or a ring system containing tertiary carbon atoms such as adamantyl derivatives. Examples of tertiary carbon atom groups include, but are not limited to, —$C(CH_3)_3$, —$CCl_3$, —C≡CPh, 1-Adamantyl and —$C(CH_3)_2(OCH_3)$. Unless otherwise stated, preferred tertiary carbon atom groups for use herein are those wherein each R is a $C_1$-$C_6$ unsubstituted hydrocarbyl group, preferably wherein each R is a $C_1$-$C_3$ alkyl group, more preferably wherein each R is methyl. In the case wherein each R is a methyl group, the tertiary carbon atom group is tert-butyl.

The rings which may be formed by any two of $R_1$-$R_3$ and $R_7$-$R_9$ vicinal to one another taken together, $R_6$ taken together with $R_7$, $R_{10}$ taken together with $R_9$, $R_{11}$ taken together with $R_{12}$ and $R_{15}$ taken together with $R_{14}$, are preferably optionally substituted $C_5$-$C_{20}$ cyclic hydrocarbyl groups, more preferably optionally substituted $C_5$-$C_{20}$ cycloaliphatic or aromatic groups, even more preferably optionally substituted $C_5$-$C_8$ cycloaliphatic or aromatic groups, especially a $C_6$ cycloaliphatic or aromatic group.

The rings which may be formed by $R_6$ taken together with $R_4$, $R_9$ taken together with $R_4$, $R_{11}$ taken together with $R_5$ and $R_{15}$ taken together with $R_5$, are preferably optionally substituted $C_6$-$C_{20}$ cyclic hydrocarbyl groups, more preferably optionally substituted $C_6$-$C_{20}$ cycloaliphatic groups, even more preferably optionally substituted $C_6$-$C_8$ cycloaliphatic groups, especially a $C_6$ cycloaliphatic group.

The term "optionally substituted $C_1$-$C_{30}$ alkyl" in relation to the $R_{12}$, $R_{13}$ and $R_{14}$ groups, and, where applicable, the $R_7$, $R_8$ and $R_9$ groups of formula (I) above means a $C_1$ to $C_{30}$ linear or branched alkyl group, which may substituted with one or more "inert" functional groups known to those skilled in the art, in particular a halide, preferably fluorine. Preferred optionally substituted alkyl groups comprise from 3 to 25 carbon atoms, more preferably from 4 to 20 carbon atoms.

Preferably, the alkyl group is an unsubstituted alkyl group. Examples of suitable "optionally substituted $C_1$-$C_{30}$ alkyl" include octadecyl, tetradecyl, dodecyl, decyl, octyl, hexyl, pentyl, tert-butyl and iso-propyl, especially tert-butyl and iso-propyl.

The term "optionally substituted $C_4$-$C_{30}$ alkyloxy" in relation to the $R_{12}$, $R_{13}$ and $R_{14}$ groups, and, where applicable, the $R_7$, $R_8$ and $R_9$ groups of formula (I) above means a $C_4$-$C_{30}$ optionally substituted alkyl group which is attached to an oxygen atom, the alkoxy group being attached to the aryl group via the oxygen atom. Preferably, the optionally substituted alkyloxy group comprises from 6 to 30 carbon atoms, more preferably from 8 to 30 carbon atoms, and most preferably from 10 to 25 carbon atoms. Preferably, the alkyloxy group is an unsubstituted alkyloxy group. Examples of suitable "optionally substituted $C_4$-$C_{30}$ alkyloxy" include eicosanoxy (which is preferred), octadecyloxy, hexadecyloxy, tetradecyloxy, dodecyloxy, decyloxy, hexyloxy, pentyloxy, butyloxy and tert-butyloxy, especially eicosanoxy, dodecyloxy, pentyloxy and tert-butyloxy.

The term "optionally substituted $C_5$-$C_{20}$ aryl" in relation to the $R_{12}$, $R_{13}$ and $R_{14}$ groups, and, where applicable, the $R_7$, $R_8$ and $R_9$ groups of formula (I) above means an aryl or heteroaryl group, comprising from 5 to 20 ring atoms and wherein one or more of the ring atoms can be substituted with one or more substituents known to those skilled in the art, preferably selected from optionally substituted hydrocarbyl, preferably $C_1$-$C_6$ alkyl, preferably methyl, and "inert" functional groups, such as halide. In a heteroaryl group, one or more of the ring atoms is a heteroatom, such as nitrogen, oxygen or sulfur, provided that the heteroatom is inert with regard to the catalytic process in which the transition metal complex is employed. Preferably the heteroaryl groups are aromatic, fully substituted or the heteroatom is fully shielded from the transition metal atom. Preferred heteroaryl groups are 1-pyrrolyl groups. Preferably all of the ring atoms are carbon atoms. Within the term "optionally substituted $C_5$-$C_{20}$ aryl" is encompassed mono- and poly-aromatic groups. Preferred optionally substituted $C_5$-$C_{20}$ aryl groups comprise from 5 to 10 ring carbon atoms, more preferably 5 or 6 ring carbon atoms. Preferably, the aryl groups are unsubstituted aryl groups, including 1-pyrrolyl groups. Most preferred are optionally substituted phenyl groups, especially phenyl.

The rings which may be formed by $R_{13}$ taken together with $R_{12}$ or $R_{14}$, and, where applicable, $R_8$ taken together with $R_7$ or $R_9$ are preferably optionally substituted $C_5$-$C_{20}$ cyclic hydrocarbyl groups, more preferably optionally substituted $C_5$-$C_{10}$ groups, even more preferably optionally substituted $C_5$-$C_8$ groups, especially $C_5$ and $C_6$ cyclic hydrocarbyl groups. Included within the term cyclic hydrocarbyl groups in relation to the rings which may be formed by $R_{13}$ taken together with $R_{12}$ or $R_{14}$, and, where applicable, $R_8$ taken together with $R_7$ are cylcoaliphatic, polycycloaliphatic, aromatic and polyaromatic groups, preferably cycloaliphatic or aromatic groups.

In one class of transition metal complexes herein, $R_{13}$ and at least one of $R_{12}$ and $R_{14}$ are independently selected from optionally substituted $C_4$-$C_{30}$ alkyl, optionally substituted $C_4$-$C_{30}$ alkyloxy and optionally substituted $C_5$-$C_{20}$ aryl, with the proviso that at least one of $R_{12}$, $R_{13}$ and $R_{14}$ is optionally substituted $C_4$-$C_{30}$ alkyloxy, and $R_8$ and at least one of $R_7$ and $R_9$ are independently selected from optionally substituted $C_4$-$C_{30}$ alkyl, optionally substituted $C_4$-$C_{30}$ alkyloxy and optionally substituted $C_5$-$C_{20}$ aryl, with the proviso that at least one of $R_7$, $R_8$ and $R_9$ is optionally substituted $C_4$-$C_{30}$ alkyloxy.

In another class of transition metal complexes herein, $R_{12}$, $R_{13}$ and $R_{14}$ are all independently selected from optionally substituted $C_4$-$C_{30}$ alkyl, optionally substituted $C_4$-$C_{30}$ alkyloxy and optionally substituted $C_5$-$C_{20}$ aryl, with the proviso that at least one of $R_{12}$, $R_{13}$ and $R_{14}$ is optionally substituted $C_4$-$C_{30}$ alkyloxy.

In another class of transition metal complexes herein, $R_7$, $R_8$, $R_9$, $R_{12}$, $R_{13}$ and $R_{14}$ are all independently selected from optionally substituted $C_4$-$C_{30}$ alkyl, optionally substituted $C_4$-$C_{30}$ alkyloxy and optionally substituted $C_5$-$C_{20}$ aryl, with the proviso that at least one of $R_{12}$, $R_{13}$ and $R_{14}$ is optionally substituted $C_4$-$C_{30}$ alkyloxy, and at least one of $R_7$, $R_8$ and $R_9$ is optionally substituted $C_4$-$C_{30}$ alkyloxy.

The bis-arylimine pyridine ligand having the formula (I) above, may be either symmetrical or non-symmetrical. The term "symmetrical" is used in relation to the four meta-positions and two para-positions of the two aryl-imino groups and defines these as such that both the substitution pattern and the substituents themselves afford two equally substituted aryl-imino groups.

Preferred transition metal complexes of the present invention comprise ligands according to formula (I), in which the following R groups appear: $R_1$-$R_3$ are hydrogen; and/or $R_4$ and $R_5$ are methyl, hydrogen, benzyl or phenyl, preferably methyl, phenyl or hydrogen, more preferably methyl.

One preferred class of transition metal complexes of the present invention comprise ligands according to formula (I), in which the following R groups appear: $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; $R_{13}$ is $C_4$-$C_{30}$ alkyloxy, preferably $C_{10}$-$C_{25}$ alkyloxy, more preferably eicosanoxy.

Another preferred class of transition metal complexes of the present invention comprise ligands according to formula (I), in which the following R groups appear: $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; $R_{13}$ is $C_4$-$C_{30}$ alkyloxy, preferably $C_{10}$-$C_{25}$ alkyloxy, more preferably eicosanoxy; $R_6$ is selected from $C_1$-$C_{30}$ alkyl, preferably $C_1$-$C_{10}$ alkyl, more preferably $C_3$-$C_6$ alkyl, most preferably tert-butyl or iso-propyl; $R_8$ and $R_{10}$ are hydrogen; and preferably $R_7$ and $R_9$ are hydrogen.

Another preferred class of transition metal complexes of the present invention comprise ligands according to formula (I), in which the following R groups appear: $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; $R_{13}$ is $C_4$-$C_{30}$ alkyloxy, preferably $C_{10}$-$C_{25}$ alkyloxy, more preferably eicosanoxy; $R_6$, $R_8$ and $R_{10}$ are independently selected from $C_1$-$C_{30}$ alkyl, preferably $C_1$-$C_{10}$ alkyl, more preferably $C_1$-$C_6$ alkyl, most preferably methyl, ethyl, iso-propyl or tert-butyl; and preferably $R_7$ and $R_9$ are hydrogen.

Another preferred class of transition metal complexes of the present invention comprise ligands according to formula (I), in which the following R groups appear: $R_{12}$ and $R_{14}$ are independently selected from $C_1$-$C_{30}$ alkyl and $C_5$-$C_{20}$ aryl, preferably $C_5$-$C_{20}$ aryl, more preferably phenyl; $R_{13}$ is $C_4$-$C_{30}$ alkyloxy, preferably $C_{10}$-$C_{25}$ alkyloxy, more preferably eicosanoxy; $R_7$ and $R_9$ are independently selected from $C_1$-$C_{30}$ alkyl, preferably $C_1$-$C_{10}$ alkyl, more preferably $C_3$-$C_6$ alkyl, most preferably iso-propyl or tert-butyl; and preferably $R_6$, $R_8$ and $R_{10}$ are hydrogen.

Another class of transition metal complexes of the present invention comprise ligands according to formula (I), in which the following R groups appear: $R_7$ and $R_9$ are independently selected from $C_1$-$C_{30}$ alkyl and $C_5$-$C_{20}$ aryl, preferably $C_5$-$C_{20}$ aryl, more preferably phenyl; $R_8$ is $C_4$-$C_{30}$ alkyloxy, preferably $C_{10}$-$C_{25}$ alkyloxy, more preferably eicosanoxy.

Another class of transition metal complexes of the present invention comprise ligands according to formula (I), in which the following R groups appear: $R_8$ independently selected from $C_1$-$C_{30}$ alkyl, preferably $C_1$-$C_{10}$ alkyl, more preferably $C_3$-$C_6$ alkyl, most preferably iso-propyl or tert-butyl; and preferably $R_6$, $R_7$, $R_9$ and $R_{10}$ are hydrogen.

In a preferred embodiment, the transition metal complex comprises a ligand according to formula (I), wherein $R_1$-$R_3$ are hydrogen, $R_4$ and $R_5$ are methyl, $R_6$, $R_8$ and $R_{10}$ are methyl, $R_7$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_5$ are hydrogen, $R_6$, $R_8$ and $R_{10}$ are methyl, $R_7$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$, $R_8$ and $R_{10}$ are methyl, $R_7$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$ and $R_{10}$ are fluorine, $R_7$, $R_8$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_5$ are hydrogen, $R_6$ and $R_{10}$ are fluorine, $R_7$, $R_8$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$ and $R_{10}$ are fluorine, $R_7$, $R_8$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$ and $R_{10}$ are chlorine, $R_7$, $R_8$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_5$ are hydrogen, $R_6$ and $R_{10}$ are chlorine, $R_7$, $R_8$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$ and $R_{10}$ are chlorine, $R_7$, $R_8$, $R_9$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$, $R_{10}$, $R_{11}$ and $R_{15}$ are hydrogen, $R_7$, $R_9$, $R_{12}$ and $R_{14}$ are phenyl and $R_8$ and $R_{13}$ is eicosanoxy.

In another preferred embodiment, the transition metal complex comprises a ligand according to formula (I), wherein $R_1$-$R_5$ are hydrogen, $R_6$, $R_{10}$, $R_{11}$ and $R_{15}$ are hydrogen, $R_7$, $R_9$, $R_{12}$ and $R_{14}$ are phenyl and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$, $R_{10}$, $R_{11}$ and $R_{15}$ are hydrogen, $R_7$, $R_9$, $R_{12}$ and $R_{14}$ are phenyl and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$ is tert-butyl, $R_7$, $R_8$, $R_9$, $R_{10}$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_5$ are hydrogen, $R_6$ is tert-butyl, $R_7$, $R_8$, $R_9$, $R_{10}$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$ is tert-butyl, $R_7$, $R_8$, $R_9$, $R_{10}$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_7$, and $R_9$ are iso-propyl, $R_6$, $R_8$, $R_{10}$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_5$ are hydrogen, $R_7$, and $R_9$ are iso-propyl, $R_6$, $R_8$, $R_{10}$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_7$, and $R_9$ are iso-propyl, $R_6$, $R_8$, $R_{10}$, $R_{11}$ and $R_{15}$ are hydrogen, $R_{12}$ and $R_{14}$ are phenyl and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_7$ is iso-propyl, $R_{10}$ is methyl, $R_6$, $R_9$, $R_{11}$ and $R_{15}$ are hydrogen, $R_{12}$ and $R_{14}$ are phenyl and $R_8$ and $R_{13}$ is eicosanoxy.

In another preferred embodiment, the transition metal complex comprises a ligand according to formula (I), wherein $R_1$-$R_5$ are hydrogen, $R_7$ is iso-propyl, $R_{10}$ is methyl, $R_6$, $R_9$, $R_{11}$ and $R_{15}$ are hydrogen, $R_{12}$ and $R_{14}$ are phenyl and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_7$ is iso-propyl, $R_{10}$ is methyl, $R_6$, $R_9$, $R_{11}$ and $R_{15}$ are hydrogen, $R_{12}$ and $R_{14}$ are phenyl and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$, $R_8$ and $R_{10}$ are methyl, $R_7$, $R_9$, $R_{11}$ and $R_{15}$ are hydrogen, $R_{12}$ and $R_{14}$ are fluorine and $R_{13}$ is eicosanoxy.

In another preferred embodiment, the transition metal complex comprises a ligand according to formula (I), wherein $R_1$-$R_5$ are hydrogen, $R_6$, $R_8$ and $R_{10}$ are methyl, $R_7$, $R_9$, $R_{11}$ and $R_{15}$ are hydrogen, $R_{12}$ and $R_{14}$ are fluorine and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$, $R_8$ and $R_{10}$ are methyl, $R_7$, $R_9$, $R_{11}$ and $R_{15}$ are hydrogen, $R_{12}$ and $R_{14}$ are fluorine and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$, $R_8$ and $R_{10}$ are methyl, $R_7$, $R_9$, $R_{11}$ and $R_{15}$ are hydrogen, $R_{12}$ and $R_{14}$ are chlorine and $R_{13}$ is eicosanoxy.

In another preferred embodiment, the transition metal complex comprises a ligand according to formula (I), wherein $R_1$-$R_5$ are hydrogen, $R_6$, $R_8$ and $R_{10}$ are methyl, $R_7$, $R_9$, $R_{11}$ and $R_{15}$ are hydrogen, $R_{12}$ and $R_{14}$ are chlorine and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$, $R_8$ and $R_{10}$ are methyl, $R_7$, $R_9$, $R_{11}$ and $R_{15}$ are hydrogen, $R_{12}$ and $R_{14}$ are chlorine and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$, $R_{10}$, $R_{11}$ and $R_{15}$ are hydrogen, $R_7$, $R_9$, $R_{12}$ and $R_{14}$ are fluorine and $R_8$ and $R_{13}$ is eicosanoxy.

In another preferred embodiment, the transition metal complex comprises a ligand according to formula (I), wherein $R_1$-$R_5$ are hydrogen, $R_6$, $R_{10}$, $R_{11}$ and $R_{15}$ are hydrogen, $R_7$, $R_9$, $R_{12}$ and $R_{14}$ are fluorine and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$, $R_{10}$, $R_{11}$ and $R_{15}$ are hydrogen, $R_7$, $R_9$, $R_{12}$ and $R_{14}$ are fluorine and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$, $R_{10}$, $R_{11}$ and $R_{15}$ are hydrogen, $R_7$, $R_9$, $R_{12}$ and $R_{14}$ are chlorine and $R_8$ and $R_{13}$ is eicosanoxy.

In another preferred embodiment, the transition metal complex comprises a ligand according to formula (I), wherein $R_1$-$R_5$ are hydrogen, $R_6$, $R_{10}$, $R_{11}$ and $R_{15}$ are hydrogen, $R_7$, $R_9$, $R_{12}$ and $R_{14}$ are chlorine and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$, $R_{10}$, $R_{11}$ and $R_{15}$ are hydrogen, $R_7$, $R_9$, $R_{12}$ and $R_{14}$ are chlorine and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are methyl, $R_6$, $R_9$, $R_{12}$ and $R_{15}$ are hydrogen, $R_7$ and $R_{14}$ are iso-propyl, $R_{10}$ and $R_{11}$ are methyl and $R_8$ and $R_{13}$ is eicosanoxy.

In another preferred embodiment, the transition metal complex comprises a ligand according to formula (I), wherein $R_1$-$R_5$ are hydrogen, $R_6$, $R_9$, $R_{12}$ and $R_{14}$ are hydrogen, $R_7$ and $R_{15}$ are iso-propyl, $R_{10}$ and $R_{11}$ are methyl and $R_8$ and $R_{13}$ is eicosanoxy.

In another preferred embodiment, the transition metal complex comprises a ligand according to formula (I), wherein $R_1$-$R_3$ are hydrogen, $R_4$ and $R_5$ are phenyl, $R_6$, $R_9$, $R_{12}$ and $R_{15}$ are hydrogen, $R_7$ and $R_{14}$ are iso-propyl, $R_{10}$ and $R_{11}$ are methyl and $R_8$ and $R_{13}$ is eicosanoxy.

The present invention also relates to a catalyst system comprising:

(a) one or more transition metal complexes defined herein; and (b) a co-catalyst compound (1) or (2) as defined and described herein The catalyst system of the present invention may also comprise one or more additional co-catalyst compounds as optional component (c).

The purpose of co-catalyst compound(s) (b) is to form an activated catalyst system.

A co-catalyst compound capable of abstracting an anion ($X^-$ group) and transferring an optionally susbstituted hydrocarbyl or hydride group to the transition metal atom (M), preferably at a temperature in the range of $-100°$ C. to $+300°$ C., is selected from alkylaluminium compounds such as alky-laluminoxane and alkylaluminium halides. Preferred compounds of this type are methylaluminoxane (MAO) and modified methylaluminoxane (MMAO).

A co-catalyst compound capable of transferring an optionally substituted hydrocarbyl or hydride group to the transition metal atom (M), preferably at a temperature in the range of $-100°$ C. to $+300°$ C., is selected from alkylaluminium compounds such as alkyl aluminoxanes, alkyl lithium compounds, Grignards, alkyl tin and alkyl zinc compounds, such as compounds of the formula $ZnR'_2$ wherein each R', which may be the same or different, is selected from hydrogen, optionally substituted $C_1$-$C_{20}$ hydrocarbyl, phenyl, Cl, Br, I, SR'', $NR''_2$, OH, OR'', CN, NC (isocyanide) wherein R'', which within the same molecule may the same or different, is $C_1$-$C_{20}$ hydrocarbyl. Preferably, R' is $C_1$-$C_{20}$ hydrocarbyl, more preferably $C_1$-$C_{20}$ alkyl, even more preferably $C_1$-$C_6$ alkyl. Suitable alkyl groups include methyl, ethyl, propyl, butyl, and the like. It is especially preferred that the R' group is a $C_1$-$C_3$ alkyl, especially ethyl. Preferred compound of this type are methylaluminoxane (MAO) and modified methylaluminoxane (MMAO).

A co-catalyst compound capable of abstracting an anion ($X^-$ group) from the transition metal atom (M), preferably at a temperature in the range of $-100°$ C. to $+300°$ C., is selected from strong neutral Lewis acids such as $SbF_5$, $BF_3$ and $Ar_3B$, wherein Ar is a strong electron-withdrawing aryl group such as $C_6F_5$ or $3,5$-$(CF_3)_2C_6H_3$ or from salts with non-coordinating anions ($NC^-$) such as tetrakis [3,5-bis(trifluoromethyl)-phenyl]borate ($BArF^-$), $(C_6F_5)_4B^-$, and anions of alkylaluminium compounds including $R_3AlX'^-$, $R_2AlClX'^-$, $RAlCl_2X'^-$, and "$RAlOX'^-$", wherein R is hydrogen, optionally substituted hydrocarbyl or an inert functional group, and X' is halide, alkoxide or oxygen. A preferred salt with a non-coordinating anion for use herein is sodium tetrakis [3,5-bis(trifluoromethyl)-phenyl]borate ($Na^+$ $BArF^-$).

Additional co-catalyst compounds (c), which may be used in addition to co-catalyst compound(s) (b), include, but are not necessarily limited to, neutral Lewis donor molecules.

The term "neutral Lewis donor molecule" as used in herein means a compound which may suitably act as a Lewis base, such as ethers, amines, sulphides and organic nitriles, for example, triethylamine or 2,6-di-tert-butylpyridine.

The ligands and transition metal complexes of the present invention may be prepared using the chemical processes and equivalent processes to those illustrated in the examples of the present invention and the references therein, as well as the processes known from WO01/58874, WO02/00339, WO02/28805 and WO 03/011876 and the references incorporated therein.

The catalyst system of the present invention may be formed by mixing together the transition metal complex or a mixture of a transition metal salt and the appropriate bis-arylimine pyridine ligand of formula (I), co-catalyst compound(s) (b), and optionally one or more additional co-catalyst compounds (c), in any order.

Conveniently, the preparation of the catalyst system of the present invention may be performed in the presence of the reaction mixture or in the presence of a chemically inert solvent which may be polar or non-polar. Preferably, the catalyst system of the present invention is prepared in the presence of the reaction mixture or in the presence of a chemically inert non-polar solvent, more preferably in the presence of a chemically inert non-polar solvent.

The use of a chemically inert non-polar solvent in the preparation of the catalyst system of the present invention may be desired for ease of handling, storage and use of the catalyst system, in particular for accurate dosing of the catalyst composition, especially during continuously operated reaction processes. Examples of suitable chemically inert non-polar solvents include o-, m- or p-xylene, toluene, benzene, pentane, isopentane, heptane, cyclohexane and isooctane, preferably the solvent is toluene, isopentane, cyclohexane and isooctane, especially toluene and isooctane.

In one embodiment, the catalyst system of the present invention is formed by combining a solution of the transition metal complex dissolved in a chemically inert non-polar solvent with a solution of the co-catalyst compound(s) (b) and optionally additional co-catalyst compound(s) (c) in a chemically inert non-polar solvent. The combining of these two separate solutions may be performed either in the presence or the absence of the reactant composition.

Alternatively, the catalyst system of the present invention is formed by combining a solution comprising a mixture of a transition metal salt and a bis-arylimine pyridine ligand of formula (I) dissolved in a chemically inert non-polar solvent with a solution of the co-catalyst compound(s) (b) and optionally additional co-catalyst compound(s) (c) in a chemically inert non-polar solvent. The combining of these two separate solutions may be performed either in the presence or the absence of the reactant composition.

In another embodiment, the catalyst system of the present invention is formed by combining a solution of the transition metal bis-arylimine pyridine complex in a chemically inert non-polar solvent, with the co-catalyst compound(s) (b) and optionally additional co-catalyst compound(s) (c), which are present in the reaction media.

Alternatively, the catalyst system of the present invention is formed by combining a mixture of a transition metal salt and a bis-arylimine pyridine ligand of formula (I) in a chemically inert non-polar solvent, with the co-catalyst compound(s) (b) and optionally additional co-catalyst compound(s) (c) which are present in the reaction media.

In another embodiment, the catalyst system of the present invention is prepared by combining all the components of the catalyst system in a chemically inert non-polar solvent.

In another embodiment, the catalyst system of the present invention is prepared by combining all the components of the catalyst system in the reaction media.

The bis-arylimine ligands of formula (I), the transition metal complexes, and the catalyst systems of the present invention are highly soluble in non-polar media, such as non-polar solvents, non-polar reactant compositions and non-polar product compositions.

By the term "highly soluble", it is meant that the specific component (e.g. bis-arylimine pyridine ligand or bis-arylimine pyridine transition metal complex) will form a clear and stable solution in non-polar media at ambient temperatures. Preferably, it is meant that the component has a solubility of at least 1 mg ml$^{-1}$, e.g. at least 5 mg ml$^{-1}$, more preferably a solubility of at least 10 mg ml$^{-1}$, e.g. at least 25 mg ml$^{-1}$, most preferably at least 50 mg ml$^{-1}$ e.g. at least 75 mg ml$^{-1}$, especially at least 100 mg ml$^{-1}$, at ambient temperatures. Typically, the solubility of the components will be less than 5 g ml$^{-1}$.

The term "clear and stable solution" in the context of the present invention, means a solution having dissolved particles with diameters between 0.1 and 1 nm, which cannot be made visual by microscopic or ultramicroscopic techniques and cannot be separated by (ultra) filtration or dialysis, or a colloidal solution, having particles with diameters between 0.1 and 0.001 µm, which do not show sedimentation.

In the context of the present invention, the term "ambient temperatures" means any temperature or temperature range within the range wherein the lower temperature is at least −20° C., more preferably at least 0° C. and most preferably at least 10° C., and the upper temperature is at most 120° C., more preferably at most 50° C. and most preferably at most 40° C.

The solution of the invention is in a non-polar medium e.g. a chemically inert non-polar solvent. The solubility of the specific component (e.g. the bis-arylimine pyridine ligand, bis-arylimine pyridine transition metal complex or catalyst system comprising it) is as described particularly above, preferably at least 5, 10 or 25 mg ml$^{-1}$, such as at least 50 or 75 mg ml$^{-1}$, especially at least 100 mg ml$^{-1}$. Examples of the non-polar media are given herein, while classes of the chemically inert non-polar solvents are the inert solvents that may be used for the co-oligomerization or oligomerization mentioned herein, namely alkanes (e.g. of 5-8 carbon atoms), alkenes (e.g. of 5-8 carbon atoms especially 1-hexene, cis/trans 2-hexene or 1-octene), cycloalkanes (e.g. of 5-7 carbon atoms) and aromatic hydrocarbons (e.g. of 6-8 carbon atoms), and more particularly those named above as chemically inert non polar solvents, especially toluene, benzene or a xylene.

Examples of non-polar reactant compositions include alpha olefin compositions, such as ethylene, propylene and $C_4$-$C_{12}$ linear and branched alpha olefins, which may optionally include impurities such as internal olefins, such as $C_4$-$C_{12}$ linear and branched internal olefins, $C_2$-$C_{12}$ paraffins and the like. The non-polar product compositions are the resultant compositions produced from the polymerization, co-polymerization, oligomerization, co-oligomerization or dimerization or alpha-olefins using the catalyst system of the present invention, and may optionally include unreacted feed olefin.

The catalyst systems of the present invention are particularly useful when incorporated in the following reactions:

polymerization or oligomerization;

co-polymerization or co-oligomerization;

trimerization; and dimerization.

The catalyst systems of the present invention are particularly useful for the polymerization or oligomerization of ethylene, the co-polymerization or co-oligomerization of ethylene and an alpha-olefin, and the dimerization of alpha-olefins having at least 3 carbon atoms under continuous process conditions.

In one preferred process of the present invention, the catalyst system of the present invention is employed for the oligomerization of ethylene.

In another preferred process of the present invention, the catalyst system of the present invention is employed in the dimerization of alpha-olefins.

The catalyst system of the present invention can be used for polymerization and oligomerization reactions when ethylene or propene is used as the feed olefin.

The term "feed olefin" used in the context of the present invention relates to the repeating unit(s) which may combine when brought into contact with the catalyst system of the present invention under polymerization, co-polymerization, oligomerization, co-oligomerization, trimerization or dimerization conditions.

The catalyst systems of the present invention can be used for co-polymerization and co-oligomerization reactions when ethylene and an alpha-olefin having at least 3 carbon atoms are used as the feed olefins, or propene and an alpha-olefin having at least 4 carbon atoms are used as the feed olefin.

The catalyst systems of the present invention can be used for dimerization reactions when an alpha-olefin having at least 3 carbon atoms is used as the feed olefin, especially the dimerization of 1-butene (e.g. present in Raffinate II) to octene.

The dimerization reaction of the present invention includes the formation of dimers of more than one alpha-olefin having at least 3 carbon atoms, wherein the alpha-olefins in the feed olefin do not have the same number of carbon atoms.

When propene is used as the feed olefin in the dimerization reaction of the present invention, the dimer product olefin may be an alpha-olefin. If an alpha-olefin is produced in the dimerization of propene, the alpha-olefin product olefin may subsequently be dimerized by another propene feed olefin, which may result in the formation of another alpha-olefin dimer product which may subsequently be dimerized, or the alpha-olefin produced in the dimerization of propene may dimerize with any other alpha-olefin present, which is not propene, and form an internal olefin product which can not be dimerized further.

A preferred feed olefin used in the co-polymerization, co-oligomerization and dimerization reactions is an alpha-olefin which has at least 4 carbon atoms. The feed olefin used for the co-polymerization, co-oligomerization and dimerization reactions preferably has at most 20 carbon atoms, more preferably at most 12 carbon atoms, most preferably at most 8 carbon atoms and especially at most 6 carbon atoms. The feed olefin of the present invention can be linear or branched. Preferably the feed olefin is linear. Preferably, the feed olefin used in the co-polymerization, co-oligomerization and dimerization reactions of the present invention is selected from propene, 1-butene, 1-pentene and 1-hexene, and mixtures thereof.

The feed olefins used in the co-polymerization, co-oligomerization and dimerization reactions of the present invention may form part of a reactant composition. Said reactant composition may optionally comprise other linear or branched alpha-olefins, linear or branched internal olefins, linear or branched paraffins and other chemically inert components such as solvents.

In one embodiment of the present invention, the feed olefin composition is an olefin composition which comprises a distillation fraction of an olefin composition, comprising alpha-olefins, internal olefins and paraffins boiling in the same temperature range, for example a raffinate II composition which is primarily composed of 1-butene and 2-butene.

The oligomerization and/or co-oligomerization reactions of the present invention may be conveniently carried out using the following conditions.

A quantity of the catalyst system of the present invention is usually employed in the oligomerization or co-oligomerization reaction mixture so as to contain from $10^{-4}$ to $10^{-9}$ gram atom of transition metal atom M per mole of ethylene or ethylene and alhpha-olefin feed olefin having at least 3 carbon atoms mixture to be reacted.

The oligomerization or co-oligomerization reaction may be most conveniently conducted over a range of temperatures from $-100°$ C. to $+300°$ C., preferably in the range of from $0°$ C. to $200°$ C., and more preferably in the range of from $50°$ C. to $150°$ C.

The oligomerization or co-oligomerization reaction may be conveniently carried out at a pressure of 0.01 to 15 MPa (0.1 to 150 bar(a)), more preferably 1 to 10 MPa (10 to 100 bar(a)), and most preferably 1.5 to 5 MPa (15 to 50 bar(a)).

The optimum conditions of temperature and pressure used for a particular catalyst system to maximise the yield of oligomer or co-oligomer, and to minimise the competing reactions such as dimerization and polymerization can be readily established by one skilled in the art.

The conditions of temperature and pressure are preferably selected to yield a product slate with a Schulz-Flory K-factor within the range of from 0.40 to 0.90, most preferably in the range of from 0.60 to 0.80. In the present invention, polymerization is deemed to have occurred when a product slate has a K-factor greater than 0.9.

The oligomerization or co-oligomerization reaction can be carried out in the gas phase or liquid phase, or mixed gas-liquid phase, depending upon the volatility of the feed olefin and product olefins.

The oligomerization or co-oligomerization reaction may be carried out in the presence of an inert solvent which may also be the carrier for the catalyst and/or feed olefin. Suitable solvents include alkanes, alkenes, cycloalkanes, and aromatic hydrocarbons. For example, solvents that may be suitably used according to the present invention include heptane, isooctane, cyclohexane, benzene, toluene, and xylene.

Reaction times of from 0.1 to 10 hours have been found to be suitable, dependent on the activity of the catalyst. The reaction is preferably carried out in the absence of air or moisture.

The oligomerization or co-oligomerization reaction may be carried out in a conventional fashion. It may be carried out in a stirred tank reactor, wherein olefin and catalyst or catalyst precursors are added continuously to a stirred tank and the feed olefin, product olefin, catalyst, and catalyst are removed from the stirred tank with the product separated and the unused feed olefin and optionally the catalyst recycled back to the stirred tank.

Alternatively, the reaction may be carried out in a batch reactor, wherein the catalyst precursors or catalyst system, and feed olefin are charged to an autoclave, and after being reacted for an appropriate time, product is separated from the reaction mixture by conventional means, such as distillation.

After a suitable reaction time, the oligomerization or co-oligomerization reaction can be terminated by rapid venting of the ethylene in order to deactivate the catalyst system.

The resulting alpha olefins have a chain length of from 4 to 100 carbon atoms, preferably 4 to 30 carbon atoms, and most preferably from 4 to 20 carbon atoms.

Product olefins can be recovered, suitably by distillation, and further separated as desired by distillation techniques dependent on the intended end use of the olefins.

The soluble transition metal complexes and compositions thereof of the type described herein, have been found to be particularly useful in dimerization of alpha-olefins having 3 carbon atoms or more, the co-oligomerization of said alpha olefin and ethylene and in the oligomerization of ethylene, in each case particularly, with the transition metal complexes and catalyst systems in solution, especially in aromatic hydrocarbon solvents such as toluene.

In the transition metal complexes used in the above dimerization reaction, the $R_1$-$R_{15}$ substituents on the bis-arylimine ligand of formula (I), X and NC$^-$ are as defined hereinabove.

In preferred transition metal complexes used in the dimerization reaction of the present invention, M is selected from any Group 4 to Group 10 transition metal. In one embodiment of the dimerization process of the present invention, M is selected from Ti, V, Cr, Mn, Fe, Co, Ni, Pd or Pt; more preferably V, Cr, Mn, Fe, Co, Ni or Pd; especially Fe, Co or Cr.

In another embodiment of the dimerization process of the present invention, M is selected from Ti, V, Cr, Mn, Ni, Pd, Rh, Ru, Mo, Nb, Zr, Hf, Ta, W, Re, Os, Ir or Pt, preferably Ti, V, Cr, Mn, Ni, Pd or Pt, more preferably V, Cr, Mn, Ni or Pd, especially Cr.

In another embodiment of the dimerization process of the present invention, M is selected from Fe or Co.

Currently used processes for ethylene oligomerization produce alpha-olefins yields with undesirably large quantities of low molecular weight olefins, which has limited value. In addition, the Fischer-Tropsch process for the production of hydrocarbons produces a certain amount of low value lower olefins, also of limited value (e.g. Raffinate II—a butene composition comprising 1-butene). Therefore processes which convert these fractions into higher value products, such as higher molecular weight linear olefins (e.g. octene) are desired (i.e. dimerization).

The dimerization reactions of the present invention are particularly suitable for any $C_3$ to $C_{12}$ alpha-olefin, especially propene, 1-butene, 1-pentene and 1-hexene and compositions containing said alpha-olefins (e.g. Raffinate II which comprises 1-butene and 2-butene).

The dimerization reaction of the present invention may be conveniently carried out using the following conditions.

A quantity of the catalyst system of the present invention is usually employed in the dimerization reaction mixture so as to contain from $10^{-3}$ to $10^{-9}$ gram atom of transition metal atom M per mole of feed olefin having at least 3 carbon atoms mixture to be reacted.

The dimerization reaction may be most conveniently conducted over a range of temperatures from −100° C. to +200° C., preferably in the range of from −50° C. to 150° C., more preferably in the range of from −10° C. to 120° C., most preferably from 10° C. to 100° C., especially from 20° C. to 90° C.

The dimerization reaction may be conveniently carried out at a pressure of 0.01 to 15 MPa (0.1 to 150 bar(a)), more preferably 0.1 to 10 MPa (1 to 100 bar(a)), and most preferably 0.1 to 5 MPa (1 to 50 bar(a)).

The optimum conditions of temperature and pressure used for a particular catalyst system to maximise the yield of linear dimers, and to minimise the competing reactions such as isomerization of the feed olefin can be readily established by one skilled in the art.

The dimerization reaction can be carried out in the gas phase or liquid phase, or mixed gas-liquid phase, depending upon the volatility of the feed olefin and product olefins.

The dimerization reaction may be carried out in the presence of an inert solvent which may also be the carrier for the catalyst system and/or feed olefin. Suitable solvents include alkanes, alkenes, cycloalkanes, and aromatic hydrocarbons. For example, solvents that may be suitably used according to the present invention include heptane, isooctane, cyclohexane, benzene, toluene, and xylene.

Reaction times of from 0.1 to 10 hours have been found to be suitable, dependent on the activity of the catalyst. The reaction is preferably carried out in the absence of air or moisture.

The dimerization reaction may be carried out in a conventional fashion. It may be carried out in a stirred tank reactor, wherein the feed olefin and catalyst system or catalyst precursors are added continuously to a stirred tank and the feed olefin and catalyst system are removed from the stirred tank with the product olefin, which may then be separated, and optionally the unused feed olefin and/or the catalyst system are recycled back to the stirred tank.

Alternatively, the reaction may be carried out in a batch reactor, wherein the catalyst system or the catalyst system precursors, and feed olefin are charged to an autoclave, and after being reacted for an appropriate time, product is separated from the reaction mixture by conventional means, such as distillation.

After a suitable reaction time, the dimerization reaction can be terminated by exposure of the catalyst composition to air or starving the reaction of feed olefin.

The product olefins produced by the dimerization process of the present invention preferably comprise at least 6 carbon atoms and at most 30 carbon atoms, more preferably at most 20 carbon atoms, and most preferably 16 carbon atoms. In one aspect of the dimerization process of the present invention, the product olefin is a linear olefin which comprises from 6 to 12 carbon atoms, preferably hexenes, octenes, decenes and dodecenes, especially octenes.

Product olefins can be recovered suitably by distillation and further separated as desired by distillation techniques dependent on the intended end use of the olefins.

The invention is illustrated in the following Examples.

EXAMPLES

General Procedures and Characterisation

All chemicals used in preparations were purchased from Aldrich and used without further purification unless mentioned otherwise.

All the operations with the catalyst systems were carried out under nitrogen atmosphere. All solvents used were dried using standard procedures.

Anhydrous toluene (99.8% purity) was dried over 4 Å molecular sieves (final water content of about 3 ppm). Isooctane (2,4,4-trimethylpentane, 99.8% purity) was dried by prolonged nitrogen purge, followed by passage over 4 Å molecular sieves (final water content of about 1 ppm). Anhydrous heptane (99.8% purity) was dried by passage over 4 Å molecular sieves (final water content of about 1 ppm).

Ethylene (99.5% purity) was purified over a column containing 4 Å molecular sieves and BTS catalyst (BASF) in order to reduce water and oxygen content to <1 ppm. Propene (99.0% purity) and 1-butene (grade 2.0, i.e. 99.0% purity) were purchased from Hoek Loos N. V., Dieren, The Netherlands, 1-pentene (99% purity) from Aldrich and 1-hexene (>99% purity) from Shell Chemicals were used without further purification.

The oligomers obtained were characterised by Gas Chromatography (GC), in order to evaluate oligomer distribution using a HP 5890 series II apparatus and the following chromatographic conditions:

Column: HP-1 (cross-linked methyl siloxane), film thickness=0.25 μm, internal diameter=0.25 mm, length 60 m (by Hewlett Packard); injection temperature: 325° C.; detection temperature: 325° C.; initial temperature: 40° C. for 10 minutes; temperature programme rate: 10.0° C./minute; final temperature: 325° C. for 41.5 minutes; internal standard: n-hexylbenzene.

Response factors for the even and odd linear α-olefins, for the internal hexenes: cis- and trans-2-hexene, and cis- and trans-3-hexene, and for the branched hexenes: 3-methyl-1-pentene and 2-ethyl-1-butene, relative to n-hexylbenzene (internal standard) were determined using a standard calibration mixture. The response factors of the branched and internal heptenes and dodecenes were assumed to be equal to the corresponding even and odd linear α-olefins.

In case of ethylene oligomerization, the yields of the $C_4$-$C_{30}$ olefins were obtained from the GC analysis, from which the K-factor and the theoretical yield of $C_4$-$C_{100}$ olefins, i.e. total oligomerization product (Total Product), were determined by regression analysis, using the $C_6$-$C_{28}$ data.

In case of oligomerization or dimerization of alpha-olefins, or co-oligomerization of ethylene and alpha-olefins, the yields of the branched and internal, even and odd olefins were determined by the same GC-method.

The relative amounts of the linear 1-hexene amongst all hexene isomers, the relative amount of 1-heptene amongst all heptene isomers, the relative amount of 1-decene amongst all decene isomers, and the relative amount of 1-dodecene amongst all dodecene isomers found from the GC analysis is used as a measure of the selectivity of the catalyst towards linear alpha-olefin formation.

The NMR data was obtained at room temperature with a Varian 300 MHz or 400 MHz apparatus.

The practical solubility of the transition metal complexes was determined at ambient temperature in the inert atmosphere of the dry box.

1 mg of solid complex was contacted with 0.5 ml of benzene-D6 in an NMR-tube (5 mm external diameter) and gently swirled. If, after 1 minute of contact between the solid complex and the solvent under swirling or shaking, it does not result in a coloured solution and the solid remains deposited, further solvent is added stepwise to a final volume of 1.0 ml. If the solvent does not become coloured and the solid remains deposited even after stepwise increase of the volume of benzene-D6 to 1.0 ml and standing at ambient temperature for 24 hours, the complex is categorised as having a solubility <1 mg/ml. If the solution becomes coloured and 1 mg of the complex dissolves in about 1 ml of solvent it is categorised as having a solubility of ca. 1 mg/ml. Likewise, for higher solubility of complexes the amount of complex is increased to 10 mg or to 100 mg and the practical solubility is estimated by stepwise (0.1-ml steps) increase of benzene-D6, starting from 0.5 ml. The solubility of the complexes was confirmed in toluene at room temperature, which yielded results similar to that of benzene-D6. The solubility of these transition metal complexes was confirmed by the possibility to measure their NMR-spectra. Deposit formation upon standing for 24 hour and also on some occasions upon centrifugation (at 2500 rpm during 30 minutes) was checked and shown to be absent for the complexes categorized as having a solubility of at least 10 mg/ml.

Transition Metal Complex and Catalyst Preparation

Example 1 (Comparative)

The 2-[1-(2,4,6-trimethylphenylimino)ethyl]-6-[1-(4-tert-butylphenylimino)ethyl]pyridine iron[II] chloride complex (1) was prepared according to the method disclosed in WO02/28805 and has the formula below:

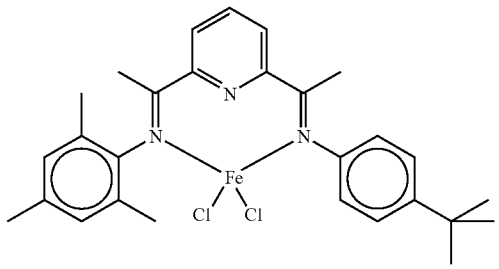

(A)

Its solubility in toluene or benzene-$D_6$ is <1 mg/ml at 20° C.

Example 2 (Comparative)

The 2-[1-(2,4,6-trimethylphenylimino)ethyl]-6-[1-(3,5-di-tert-butylphenylimino)ethyl]pyridine iron[II] chloride complex which was prepared according to the method described below:

Preparation of 2-[1-(2,4,6-trimethylphenylimino) ethyl]-6-[1-(3,5-di-tert-butylphenylimino)ethyl]pyridine, (B)

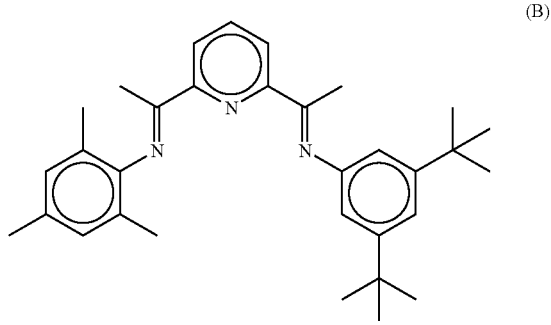

(B)

2-[1-(2,4,6-trimethylphenylimino)ethyl]-6-acetylpyridine (1.3 g, 4.64 mmol), prepared according to the method disclosed in WO02/28805, and 3,5-di-tert-butylaniline (1 g, 4.87 mmol) were dissolved in 100 ml of toluene. To this solution, 4 Å molecular sieves were added. After standing for 2 days the mixture was filtered. The solvent was removed in vacuo. The residue was washed with methanol and crystallised from ethanol. Yield 1.1 g (51%) of 2-[1-(2,4,6-trimethylphenylimino)ethyl]-6-[1-(3,5-di-tert-butylphenylimino)ethyl]pyridine.

$^1$H-NMR (CDCl$_3$) δ 8.43 (d, 1H, Py-H$_m$), 8.37 (d, 1H, Py-H$_m$), 7.87 (t, 1H, Py-H$_p$), 7.16 (t, 1H, ArH), 6.89 (s, 2H, ArH), 6.69 (d, 2H, ArH), 2.42 (s, 3H, Me), 2.29 (s, 3H, Me), 2.22 (s, 3H, Me), 2.01 (s, 6H, Me), 1.33 (s, 18H, Bu$^t$).

Preparation of 2-[1-(2,4,6-trimethylphenylimino) ethyl]-6-[1-(3,5-di-tert-butylphenylimino)ethyl]pyridine iron[II] chloride complex, (C)

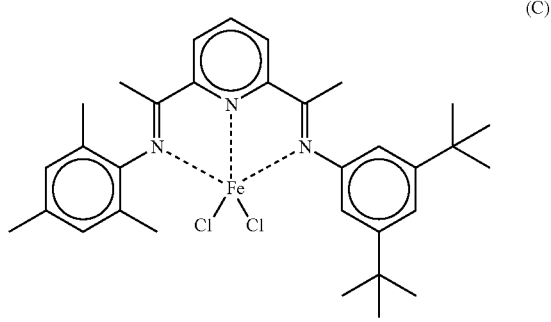

(C)

In an inert atmosphere a solution of 400 mg diimine (0.855 mmol) in 20 ml dichloromethane was added to 100 mg FeCl$_2$ (0.789 mmol) in 30 ml dichloromethane. The mixture was stirred for 16 hours. A small amount of precipitate was removed by centrifugation. Pentane (40 ml) was added to the solution. The blue precipitate was isolated by filtration and dried in vacuo. Yield 0.420 g (90%) of iron complex C.

$^1$H-NMR (Cl$_2$CDCDCl$_2$, broad signals) δ 78.6 (1H, Py-H$_m$), 76.8 (1H, Py-H$_m$), 29.7 (1H, Py-H$_p$), 20.9 (3H, Me), 18.3 (6H, Me), 15.2 (2H, ArH), 0.7 (18H, Bu$^t$), −4.1 (3H, MeC=N), −11.5 (1H, ArH), −15.6 (2H, o-ArH), −30.7 (3H, MeC=N).

Its solubility in toluene or benzene-D$_6$ is estimated at <1 mg/ml at 20° C.

Examples 3-10

Alternatively, the catalysts used in the experiments below were 2-[1-(2,4,6-trimethylphenylimino)ethyl]-6-[1-(4-eicosanoxy-3,5-diphenylphenylimino)ethyl]pyridine iron [II] dichloride complex, 2-[1-(2,4,6-trimethylphenylimino) ethyl]-6-[1-(4-eicosanoxy-3,5-diphenylphenylimino)ethyl] pyridine cobalt[II] dichloride complex, 2-[1-(2,4,6-trimethylphenylimino)ethyl]-6-[1-(4-eicosanoxy-3,5-diphenylphenylimino)ethyl]pyridine cobalt[II] chloride tetrakis[3,5-bis[trifluoromethyl)phenyl]borate, 2-[1-(2,4,6-trimethylphenylimino)ethyl]-6-[1-(4-eicosanoxy-3,5-diphenylphenylimino)ethyl]pyridine chromium[III] trichloride complex, 2,6-bis [1-(4-eicosanoxy-3,5-diphenylphenylimino)ethyl]pyridine iron[II] dichloride complex, 2,6-bis[1-(4-eicosanoxy-3,5-diphenylphenylimino)ethyl]pyridine cobalt[II] dichloride complex, 2,6-bis[1-(4-eicosanoxy-3,5-diphenylphenylimino)ethyl]pyridine chromium[III] trichloride complex and 2-[1-(2-tert-butylphenylimino)ethyl]-6-[1-(4-eicosanoxy-3,5-diphenylphenylimino)ethyl]pyridine cobalt[II] chloride complex, which were prepared according to the methods described below:

Preparation of 4-hydroxy-3,5-diphenylacetanilide

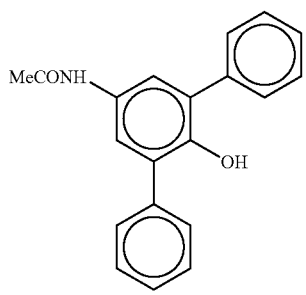

To 4-hydroxy-3,5-diphenylaniline (4 g, 15.3 mmol) in 30 ml of ethanol was added 1.6 ml of acetic anhydride. The reaction was stirred for 16 hours. The resulting mixture was poured into water. The pink product (6 g) was isolated by filtration, washed with water, dried and used without further purification.

$^1$H-NMR (CDCl$_3$, selected data) δ 5.31 (s, OH), 2.16 (s, Me).

Preparation of 4-eicosanoxy-3,5-diphenylacetanilide

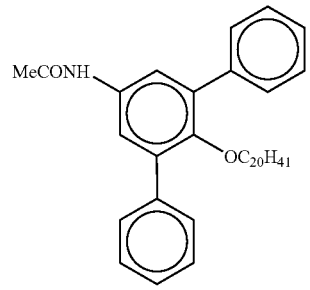

A mixture of 4-hydroxy-3,5-diphenylacetanilide(6 g), 1-bromoeicosane and 10 g potassium carbonate was refluxed in acetone (70 ml) for 16 hours. The reaction mixture was poured into water. The product was isolated by filtration, washed with water and dried. Crystallisation from pentane yielded 7.2 g of 4-eicosanoxy-3,5-diphenylacetanilide as a white solid.

$^1$H-NMR (CDCl$_3$, selected data) δ 3.13 (t, CH$_2$O), 2.17 (s, Me).

Preparation of 4-eicosanoxy-3,5-diphenylaniline

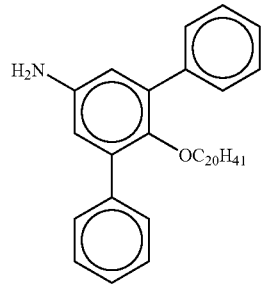

To 4-eicosanoxy-3,5-diphenylacetanilide (7.2 g) was added 24 g NaOH in 30 ml H$_2$O and 40 ml ethanol. The resulting mixture was refluxed for 16 hours. The reaction mixture was poured on ice. The product was isolated by filtration and washed with water. Crystallisation from ethanol yielded 5.9 g (10.9 mmol) of 4-eicosanoxy-3,5-diphenylaniline as a white solid.

$^1$H-NMR (CDCl$_3$) δ 7.27-7.63 (m, 10H, ArH), 6.67 (s, 2H, ArH), 3.60 (br s, 2H, NH$_2$), 3.09 (t, 2H, CH$_2$O), 0.8-1.4 (m, 39H, alkyl).

Preparation of 2-[1-(2,4,6-trimethylphenylimino) ethyl]-6-[1-(4-eicosanoxy-3,5-diphenylphenylimino) ethyl]pyridine, (D)

(D)

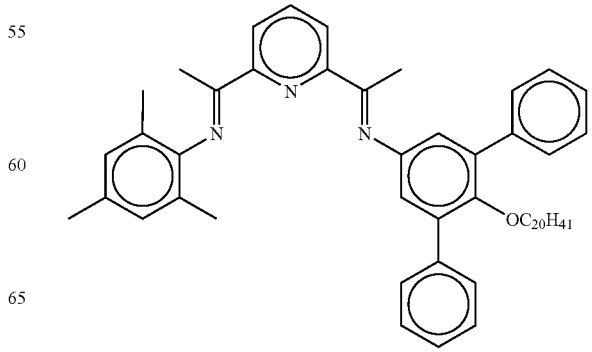

2-[1-(2,4,6-trimethylphenylimino)ethyl]-6-acetyl pyridine (3 g, 10.7 mmol), prepared according to the method disclosed in WO02/28805, and 4-eicosanoxy-3,5-diphenylaniline (5.8 g, 10.7 mmol) were dissolved in 200 ml of toluene. To this solution, 4 Å molecular sieves were added. After standing for 1 day the mixture was filtered. The solvent was removed in vacuo. The residue was crystallised from cold ethanol. The product, D, was isolated as a yellow treacle (6.5 g, 8.1 mmol, 76%) after drying at 60° C. in vacuo.

$^1$H-NMR (CDCl$_3$) δ 8.45 (d, 1H, Py-H$_m$), 8.37 (d, 1H, Py-H$_m$), 7.89 (t, 1H, Py-H$_p$), 7.67 (d, 4H, ArH), 7.1-7.5 (m, 16H, ArH), 6.90 (s, 2H, ArH), 6.86 (s, 2H, ArH), 3.19 (t, 2H, CH$_2$O), 2.51 (s, 3H, Me), 2.29 (s, 3H, Me), 2.22 (s, 3H, Me), 2.01 (s, 6H, Me), 0.8-1.4 (m, 39H, alkyl).

Example 3

Preparation of 2-[1-(2,4,6-trimethylphenylimino) ethyl]-6-[1-(4-eicosanoxy-3,5-diphenylphenylimino) ethyl]pyridine iron[II] dichloride complex, (E)

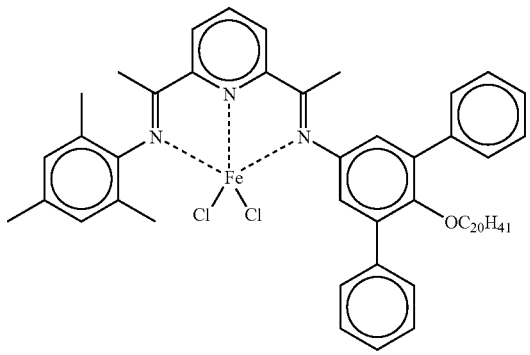

(E)

In an inert atmosphere a solution of 5 g above-described diimine (D) in 20 ml dichloromethane was added to 788 mg FeCl$_2$ in 30 ml dichloromethane. The mixture was stirred for 16 hours. The solution was filtered, and the solvent was removed in vacuo. The resulting green blue product was washed with pentane, isolated by filtration and dried in vacuo. Yield 5 g (86%) of iron complex E.

$^1$H-NMR (CD$_2$Cl$_2$, broad signals, selected data) δ 81.4 (1H, Py-H$_m$), 80.5 (1H, Py-H$_m$), 21.1 (3H, Me), 17.3 (6H, Me), 16.0 (2H, ArH), 0.21 (3H, Me), −13.8 (2H, ArH), −30.4 (3H, Me).

Its solubility in toluene or benzene-D$_6$ is estimated at ca. 50 mg/ml at 20° C.

Example 4

Preparation of 2-[1-(2,4,6-trimethylphenylimino) ethyl]-6-[1-(4-eicosanoxy-3,5-diphenylphenylimino) ethyl]pyridine cobalt[II] dichloride complex, (F)

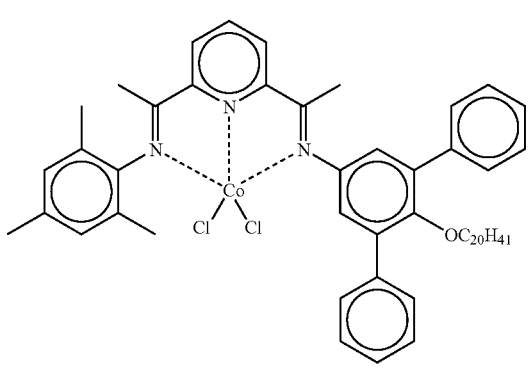

(F)

In an inert atmosphere a solution of 1.44 g (1.79 mmol) diimine D, (Mes/Sol20), in 10 ml dichloromethane was added to 220 mg CoCl$_2$ (1.69 mmol) in 10 ml dichloromethane. The mixture was stirred for 16 hours. After filtration the solution was concentrated by removing part of the solvent in vacuo. The product was precipitated from the resulting solution (~5 ml) by addition of 15 ml pentane. The yellow brown solid was isolated by centrifugation, washed with pentane and dried in vacuo. Yield 1.25 g (79%) of cobalt complex F.

$^1$H-NMR (CD$_2$Cl$_2$, broad signals, selected data) δ 106.5 (1H, Py-H$_m$), 105.6 (1H, Py-H$_m$), 12.8 (1H, Py-H$_p$), 11.8 (3H, Me), 3.4 (2H), 2.9 (4H), 0.1 (2H), −0.2 (2H), −0.7 (2H), −1.5 (2H), −1.8 (2H), −2.4 (2H), −10.5 (3H, Me), −16.6 (6H, Me), −60.9 (2H, ArH).

Its solubility in toluene or benzene-D$_6$ is estimated at 50 mg/ml at 20° C.

Example 5

Preparation of 2-[1-(2,4,6-trimethylphenylimino) ethyl]-6-[1-(4-eicosanoxy-3,5-diphenylphenylimino) ethyl]pyridine cobalt[II] chloride tetrakis[3,5-bis [trifluoromethyl)phenyl]borate, (G)

In an inert atmosphere a 313 mg (0.353 mmol) of sodium tetrakis[3,5-bis(trifluoromethyl)phenyl]borate (ABCR GmbH & Co, Karlsruhe, Germany) was added to a solution of 330 mg (0.353 mmol) cobalt complex F in 20 ml toluene. The solution was stirred for 1 hour at room temperature. After removing the precipitate by centrifugation, the solvent was removed in vacuo. The resulting oil was washed three times with pentane. After drying in vacuo, the product was isolated as a yellowish solid (560 mg, 90%).

Its solubility in toluene or benzene-D$_6$ is estimated at ca. 10 mg/ml at 20° C.

Example 6

Preparation of 2-[1-(2,4,6-trimethylphenylimino) ethyl]-6-[1-(4-eicosanoxy-3,5-diphenylphenylimino) ethyl]pyridine chromium[III] trichloride complex, (H)

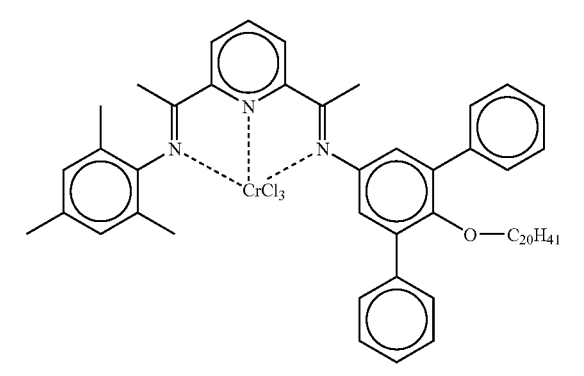

(H)

In an inert atmosphere a solution of 439 mg (0.54 mmol) diimine D in 10 ml dichloromethane was added to 195 mg (0.52 mmol) chromium[III] chloride tetrahydrofuran complex, $CrCl_3(THF)_3$ in 10 ml dichloromethane. The mixture was stirred for 4 hours. The solution was filtrated. The solution was concentrated (5 ml) by removing solvent vacuo. Pentane (20 ml) was added. The resulting green precipitate was washed with pentane and dried in vacuo. Yield 0.4 g (80%) of the chromium complex, H.

Its solubility in toluene or benzene-$D_6$ is estimated at ca. 1 mg/ml at 20° C.

Preparation of 2,6-bis[1-(4-eicosanoxy-3,5-diphenylphenylimino)ethyl]pyridine, (J)

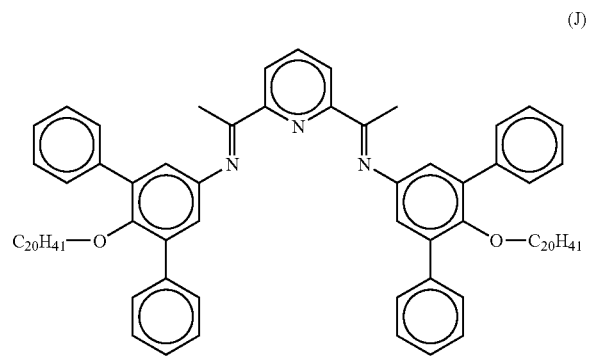

(J)

Diacetylpyridine (1.43 g, 8.77 mmol and 4-eicosanoxy-3,5-diphenylaniline (9.5 g, 17.53 mmol) were dissolved in 400 ml of toluene. To this solution, 4 Å molecular sieves were added. After standing for 1 week, further 4 Å molecular sieves were added and the mixture was filtered. Most of the solvent was removed in vacuo. On standing a red precipitate was formed. The product, J, was isolated (5.52 g, 51%).

$^1$H-NMR (CDCl$_3$) δ 8.35 (d, 2H, Py-H$_m$), 7.88 (t, 1H, Py-H$_p$), 7.66 (d, 8H, ArH), 7.3-7.5 (m, 12H, ArH), 6.86 (s, 4H, ArH), 3.19 (t, 4H, CH$_2$O), 2.50 (s, 6H, Me), 0.8-1.4 (m, 39H, alkyl).

Example 7

Preparation of 2,6-bis[1-(4-eicosanoxy-3,5-diphenylphenylimino)ethyl]pyridine iron [II] dichloride complex, (K)

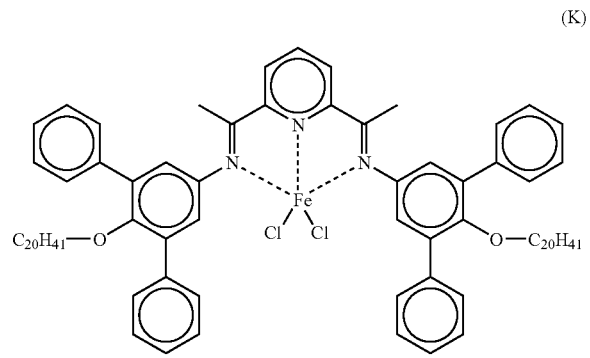

(K)

In an inert atmosphere a solution of 4 g (3.3 mmol) diimine J in 20 ml dichloromethane was added to 419 mg (3.3 mmol) FeCl$_2$ in 20 ml dichloromethane. The mixture was stirred for 48 hours. The purple blue solution was filtrated. The solvent was removed in vacuo. The resulting dark oily product was washed with pentane and dried in vacuo. Yield 3.5 g (79%) of the iron complex K.

$^1$H-NMR (C$_6$D$_6$, broad signals, selected data) δ 70.5 (2H, Py-H$_m$), −13.4 (4H, ArH), −26.2 (6H, Me).

Its solubility in toluene or benzene-$D_6$ is estimated at ca. 100 mg/ml at 20° C.

Example 8

Preparation of 2,6-bis[1-(4-eicosanoxy-3,5-diphenylphenylimino)ethyl]pyridine cobalt[II] dichloride complex, (L)

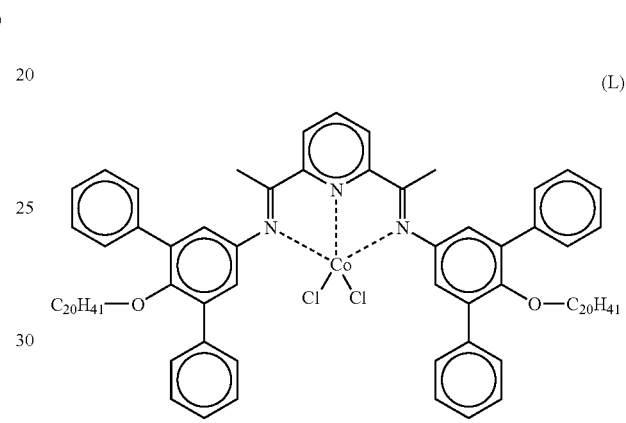

(L)

In an inert atmosphere a solution of 40 mg (33 μmol) diimine J in 2 ml dichloromethane was added to 4 mg CoCl$_2$. The mixture was stirred for 5 hours. The solution was filtrated. The solvent was removed in vacuo. The product was washed with pentane and dried in vacuo. Yield 25 mg of the cobalt complex L.

$^1$H-NMR (C$_6$D$_6$, broad signals, selected data) δ 103 (2H, Py-H$_m$), −10 (6H, Me), −50 (4H, ArH).

Its solubility in toluene or benzene-$D_6$ is estimated at ca. 100 mg/ml at 20° C.

Example 9

Preparation of 2,6-bis[1-(4-eicosanoxy-3,5-diphenylphenylimino)ethyl]pyridine chromium[III] trichloride complex, (M)

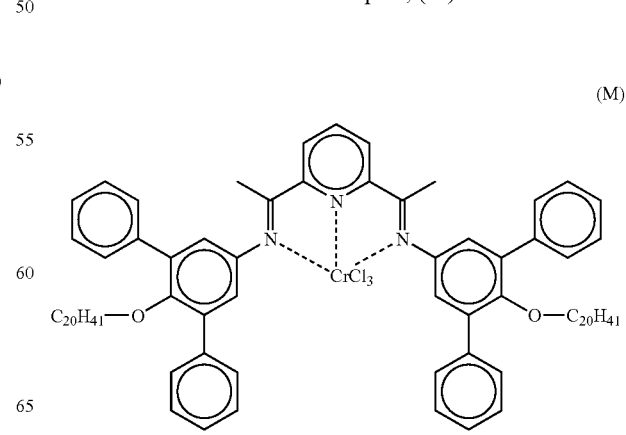

(M)

In an inert atmosphere a solution of 0.84 g (0.92 mmol) diimine J in 10 ml dichloromethane was added to 0.25 g (0.66 mmol) CrCl$_3$(THF)$_3$ in 10 ml dichloromethane. The mixture was stirred for 4 hours. The solution was filtrated. The solution was concentrated (5 ml) by removing solvent vacuo. Pentane (20 ml) was added. The resulting green precipitate was washed with pentane and dried in vacuo. Yield 0.6 g (84%) of the chromium complex M.

Its solubility in toluene or benzene-D$_6$ is estimated at ca. 50 mg/ml at 20° C.

Preparation of 2-[1-(2-tert-butylphenylimino)ethyl]-6-[1-(4-eicosanoxy-3,5-diphenylphenylimino)ethyl] pyridine, (N)

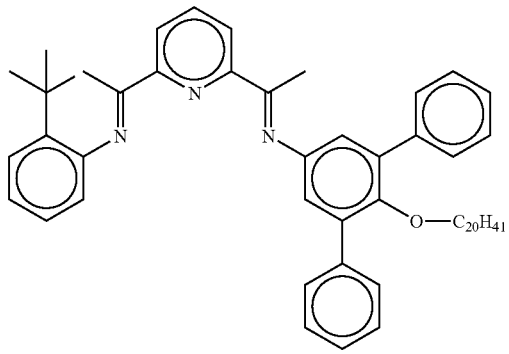

(N)

2-[1-(2-tert-butylphenylimino)ethyl]-6-acetylpyridine (487 mg, 1.65 mmol), prepared according to the method described in WO 02/28805, and 4-eicosanoxy-3,5-diphenylaniline (900 mg, 1.65 mmol) were dissolved in 50 ml of toluene. To this solution, 4 Å molecular sieves were added. After standing for 1 day the mixture was filtered. The solvent was removed in vacuo. The residue was crystallised from ethanol. The product N was isolated as an yellow solid (600 mg, 0.73 mmol, 44%).

$^1$H-NMR (CDCl$_3$) δ 8.38 (dd, 2H, Py-H$_m$), 7.90 (t, 1H, Py-H$_p$), 6.5-7.7 (m, 16H, ArH), 3.21 (t, 2H, CH$_2$O), 2.52 (s, 3H, Me), 2.40 (s, 3H, Me), 1.37 (s, 9H, t-Bu), 0.8-1.35(m, 39H, alkyl).

Example 10

Preparation of 2-[1-(2-tert-butylphenylimino)ethyl]-6-[1-(4-eicosanoxy-3,5-diphenylphenylimino)ethyl] pyridine cobalt[II] chloride complex, (O)

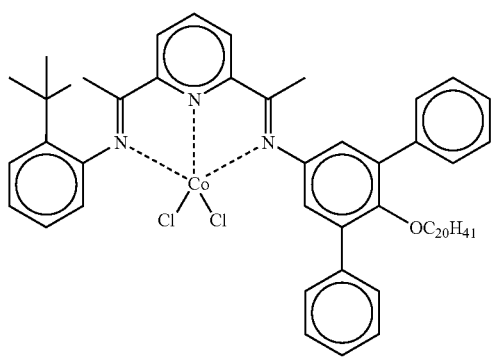

(O)

In an inert atmosphere a solution of 300 mg (0.365 mmol) diimine N in 10 ml dichloromethane was added to 40 mg CoCl$_2$ (0.308 mmol) in 5 ml dichloromethane. The mixture was stirred for 16 hours. After filtration the solution was concentrated by removing part of the solvent in vacuo. The product formed a jelly after addition of 10 ml pentane to the resulting solution (~2 ml). A yellowish brown solid was isolated by centrifugation, washing with pentane and drying in vacuo. Yield 234 mg (80%) of the cobalt complex O.

$^1$H-NMR(C$_6$D$_6$, broad signals, selected data) δ 113 (1H, Py-H$_m$), 112 (1H, Py-H$_m$), 18 (1H, Py-H$_p$), -10.8 (9H, t-Bu), -56.0 (2H, ArH), -85.6 (1H, ArH).

Its solubility in toluene or benzene-D$_6$ is estimated at ca. 50 mg/ml at 20° C.

Example 11 (Comparative)

Preparation of 4-hydroxy-2-methylacetanilide

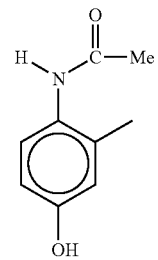

5.0 g (40.6 mmol) 4-hydroxy-2-methylaniline was taken up in 120 ml ethanol to give a cloudy, pale orange suspension. To the stirred mixture was added dropwise 4.0 ml (4.3 g, 42.3 mmol) acetic anhydride, causing the suspension to dissolve. The solution was left stirring overnight. All volatiles were subsequently removed under reduced pressure at 80° C., followed by rapid washing with 100 ml water, followed by drying under vacuum. 3.85 g (58% yield) light brown solid recovered.

Preparation of 4-eicosanoxy-2-methylaniline

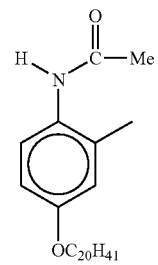

1.51 g (9.1 mmol) 4-hydroxy-2-methylacetanilide was dissolved in 100 ml acetone. To this was added 6.54 g (45 mmol, 5 eq.) potassium carbonate, and the resulting suspension stirred vigorously. To this was added 3.65 g (10.1 mmol) 1-bromoeicosane, and the reaction mixture was then heated to reflux for 22 hours. After cooling to room temperature, 500 ml deionised water was added and the solution stirred vigorously. The suspension was filtered under vacuum, and the white solid formed was dried under vacuum at 75° C. overnight. 3.72 g of the product (a white powder) was recovered (92% yield).

Preparation of 4-eicosanoxy-2-methylaniline

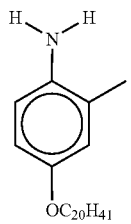

9.22 g (0.02 mol) 4-eicosanoxy-2-methylacetanilide was slurried in a solution of 18.3 g (0.45 mol) sodium hydroxide in 30 ml water and 40 ml ethanol. Under stirring it was heated to reflux and kept refluxing for 40 hours. The resulting two-phase liquid system was cooled and poured over 500 ml crushed ice, and stirred. Filtration of the white solid product and washing with 2×25 ml deionised water afforded a product, which was dried in the vacuum oven (5.4 g, 67% yield).

Preparation of 2,6-bis[1-(4-eicosanoxy-2-methylphenylimino)ethyl]pyridine

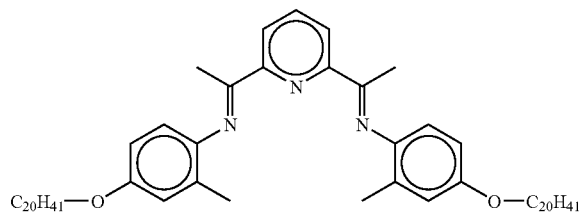

10.0 g (25 mmol) 4-eicosanoxy-2-methylaniline was reacted under stirring with 2.3 g (14 mmol) 2,6-diacetylpyridine in the presence of 29 g 4 Å molecular sieves in 250 ml of refluxing toluene for 20 h. Subsequently the compound was filtered while hot, and volatiles removed from residue under reduced pressure. It was then washed with hot ethanol (300 ml) to give a yellow solid, which was dried in the vacuum oven (9.1 g, 69% yield).

$^1$H-NMR (CDCl$_3$ after dissolving by heating) δ 8.37 (d, 2H, Py-H$_m$), 7.86 (t, 1H, Py-H$_p$), 6.82 (d, 2H, ArH), 6.75 (dd, 2H, ArH), 6.61 (d, 2H, ArH), 3.95 (t, 4H, CH$_2$O), 2.36 (s, 6H, Me), 2.12 (s, 6H, Me), 1.78 (m, 4H), 1.0-1.6 (m, 68H), 0.88 (t, 6H, Me).

Preparation of 2,6-bis[1-(4-eicosanoxy-2-methylphenylimino)ethyl]pyridine iron[II] chloride complex

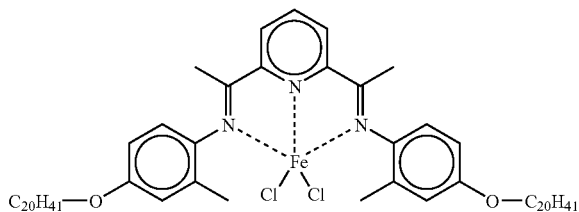

110 mg (0.12 mmol) 2,6-bis[1-(4-eicosanoxy-2-methylphenylimino)ethyl]pyridine was reacted under stirring with 35 mg (0.28 mmol) FeCl$_2$ in 10 ml dichloromethane in the dry box for 16 hours at ambient temperature. The resulting green suspension was centrifuged, and the supernatant decanted. Volatiles were then removed under reduced pressure to afford a green powder (54 mg, 42% yield).

$^1$H-NMR (CD$_2$Cl$_2$, broad signals, selected data) δ 78.2 (2H, Py-H$_m$), 39 and 31 (1H, Py-H$_p$), 19.5 and 16.8 (6H, MeAr), 40.9 and 41.2 (2H, ArH), −22.7 and −26.1 (6H, Me).

Its solubility in toluene or benzene-D$_6$ is estimated at <1 mg/ml at 20° C.

Example 12

Preparation of 2,6-bis[1-(2-methyl-4-eicosanoxy-5-isopropylphenylimino)ethyl]pyridine

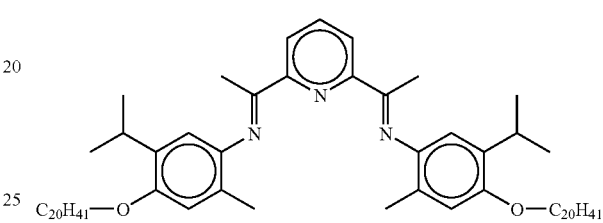

The title compound was prepared by condensation of 2-methyl-4-eicosanoxy-5-isopropylaniline with 2,6-diacetylpyridine in the presence of 4 Å molecular sieves in refluxing toluene for 20 hours, similarly to the preparation of 2,6-bis[1-(4-eicosanoxy-2-methylphenylimino)ethyl]pyridine, described above.

To that end 2-methyl-4-hydroxy-5-isopropylaniline (available from Specs, Delftechpark 30, 2628 XH Delft, The Netherlands) was converted to 2-methyl-4-eicosanoxy-5-isopropylaniline by acetylation of the amino group, followed by alkylation of the hydroxy group by reaction with 1-bromoeicosane and finally by removal of the acetyl group of amide functional group, similarly to the above-described preparation of 4-eicosanoxy-2-methylaniline.

$^1$H-NMR (CDCl$_3$) δ 8.38 (d, 2H, Py-H$_m$), 7.85 (t, 1H, Py-H$_p$), 6.72 (s, 2H, ArH), 6.56 (s, 2H, ArH), 3.95 (t, 4H, CH$_2$O), 3.15 (m, 2H, CH), 2.36 (s, 6H, Me), 2.11 (s, 6H, Me), 1.78 (m, 4H), 1.2-1.6 (m), 1.2 (d, Me), 0.88 (t, 6H, Me).

Preparation of 2,6-bis[1-(2-methyl-4-eicosanoxy-5-isopropylphenylimino)ethyl]pyridine iron (II) dichloride

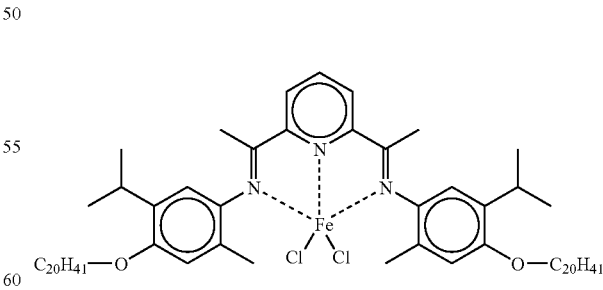

The iron complex was prepared from 2,6-bis(1-(2-methyl-4-eicosanoxy-5-isopropylphenylimino)ethyl]pyridine and FeCl$_2$ in dichloromethane.

$^1$H-NMR (CD$_2$Cl$_2$, broad signals, selected data) δ 75.9 (2H, Py-H$_m$), 42.0 and 41.2 (1H, Py-H$_p$), 21.3 and 20.2 (6H, MeAr), −12.4 and −20.9, (2H, ArH), −26.0 (6H, Me).

After removing the CD$_2$Cl$_2$ the product is soluble in C$_6$D$_6$:

$^1$H-NMR (very broad signals, selected data) δ 65 (Py-H$_m$), 23 (MeAr), −37 (Me).

Its solubility in toluene or benzene-D$_6$ is estimated at ca. 10 mg/ml at 20° C.

Example 13 (Comparative)

Preparation of 4-propoxy-3,5-diphenylacetanilide

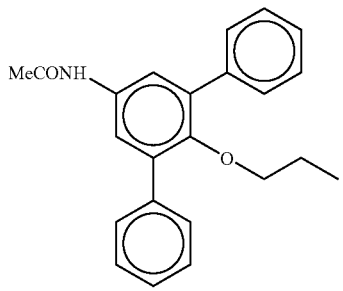

A mixture of 4-hydroxy-3,5-diphenylacetanilide (3.45 g), 1-bromopropane (1.4 g) and 4.8 g potassium carbonate was refluxed in acetone (50 ml) for 16 hours. The reaction mixture was poured into water. The product was isolated by filtration, washed with water and dried. Yield 3.8 g of 4-propoxy-3,5-diphenylacetanilide.

$^1$H-NMR (CDCl$_3$) δ 7.1-7.7 (m, ArH) 3.10 (t, 2H, CH$_2$O), 2.14 (s, Me), 1.16 (m, 2H, CH$_2$), 0.49 (t, 3H, Me).

Preparation of 4-propoxy-3,5-diphenylaniline

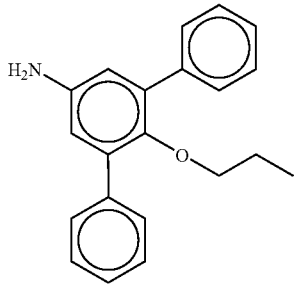

To 4-propoxy-3,5-diphenylacetanilide (3.8 g) was added 22.5 g NaOH in 30 ml H$_2$O and 40 ml ethanol. The resulting mixture was refluxed for 16 hours. The reaction mixture was poured on ice. The product was isolated as an oil after washing with water.

$^1$H-NMR (CDCl$_3$) δ 7.3-7.7 (m, 10H, ArH), 6.68 (s, 2H, ArH), 3.61 (br s, 2H, NH$_2$), 3.06 (t, 2H, CH$_2$O), 1.13 (m, 2H, CH$_2$), 0.48 (t, 3H, Me).

Preparation of 2-[1-(2,4,6-trimethylphenylimino) ethyl]-6-[1-(4-propoxy-3,5-diphenylphenylimino) ethyl]pyridine

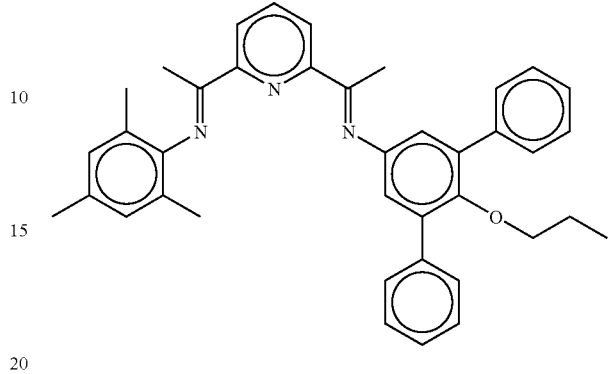

2-[1-(2,4,6-trimethylphenylimino)ethyl]-6-acetylpyridine (387 mg, 1.38 mmol) and 4-propoxy-3,5-diphenylaniline (440 mg, 1.45 mmol) were dissolved in 50 ml of toluene. To this solution, 4 Å molecular sieves were added. After standing for 1 day the mixture was filtered. The solvent was removed in vacuo. The residue was crystallised from cold ethanol. The product was isolated as a yellow treacle (700 mg) and used as such.

$^1$H-NMR (CDCl$_3$) δ 8.45 (d, 1H, Py-H$_m$), 8.37 (d, 1H, Py-H$_m$), 7.89 (t, 1H, Py-H$_p$), 7.68 (d, 4H, ArH), 7.1-7.5 (m, 16H, ArH), 6.90 (s, 2H, ArH), 6.87 (s, 2H, ArH), 3.17 (t, 2H, CH$_2$O), 2.52 (s, 3H, Me), 2.30 (s, 3H, Me), 2.23 (s, 3H, Me), 2.02 (s, 6H, Me), 1.20 (m, 2H, CH$_2$), 0.54 (t, 3H, Me).

Preparation of 2-[1-(2,4,6-trimethylphenylimino) ethyl]-6-[1-(4-propoxy-3,5-diphenylphenylimino) ethyl]pyridine cobalt[II] chloride complex

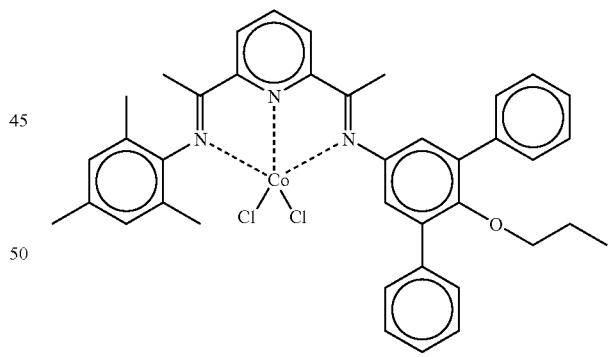

In an inert atmosphere a solution of 675 mg diimine in 20 ml dichloromethane was added to 140 mg CoCl$_2$ in 10 ml dichloromethane. The mixture was stirred for 16 hours. The solution was filtrated. The solvent was removed in vacuo. The resulting brown product was washed with pentane, isolated by filtration and dried in vacuo. Yield 700 mg of cobalt complex.

$^1$H-NMR (CD$_2$Cl$_2$, broad signals, selected data) δ 103.0 (1H, Py-H$_m$), 98.5 (1H, Py-H$_m$), −18.1 (6H, ArMe), −62.8 (2H, ArH).

Its solubility in toluene or benzene-D$_6$ is estimated at <1 mg/ml at 20° C.

Example 14 (Comparative)

Preparation of 2-[1-(2,4,6-trimethylphenylimino)ethyl]-6-[1-(4-hydroxy-3,5-diphenylphenylimino)ethyl]pyridine

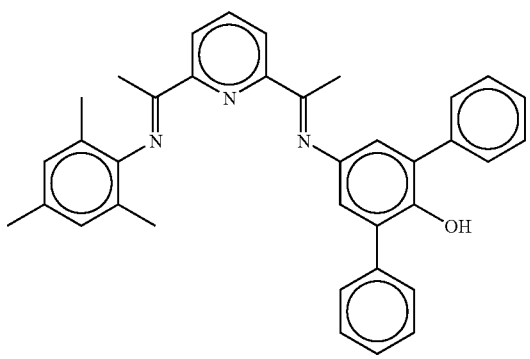

The title compound was prepared by condensation of 4-hydroxy-3,5-diphenylaniline with 2-[1-(2,4,6-trimethylphenylimino)ethyl]-6-acetylpyridine, prepared according to the method disclosed in WO02/28805, in toluene, using 4 Å molecular sieves, similarly to the above-described preparation of 2-[1-(2,4,6-trimethylphenylimino)ethyl]-6-[1-(4-propoxy-3,5-diphenylphenylimino)ethyl]pyridine.

$^1$H-NMR (CD$_2$Cl$_2$) δ 8.43 (d, 1H, Py-H$_m$), 8.35 (d, 1H, Py-H$_m$), 7.90 (t, 1H, Py-H$_p$) 7.62 (d, 4H, ArH), 7.50 (t, 4H, ArH), 7.42 (m, 2H, ArH), 6.89 (s, 2H, ArH), 6.83 (s, 2H, ArH), 2.52 (s, 3H, Me), 2.28 (s, 3H, Me), 2.21 (s, 3H, Me), 1.98 (s, 6H, Me).

Preparation of 2-[1-(2,4,6-trimethylphenylimino)ethyl]-6-[1-(4-hydroxy-3,5-diphenylphenylimino)ethyl]pyridine iron (II) dichloride

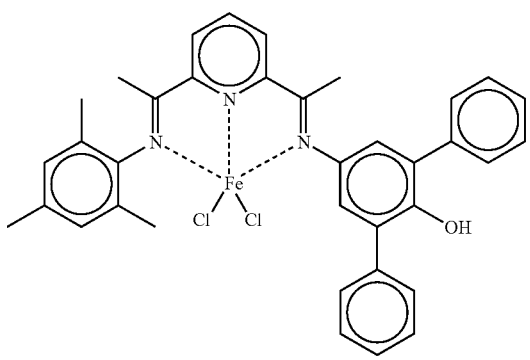

The iron complex was prepared from 2-[1-(2,4,6-trimethylphenylimino)ethyl]-6-[1-(4-hydroxy-3,5-diphenylphenylimino)ethyl]pyridine and FeCl$_2$ in dichloromethane.

$^1$H-NMR (CD$_2$Cl$_2$, broad signals, selected data) δ 82.6 (1H, Py-H$_m$), 82.3 (1H, Py-H$_m$), 21.0 (3H, Me), 18.5 (6H, Me), −4.0 (3H, Me), −18 (2H, ArH), −31.3 (3H, Ar).

Its solubility in toluene or benzene-D$_6$ is estimated at <1 mg/ml at 20° C.

Co-Catalysts

The first co-catalyst compound used in the dimerization or oligomerization experiments below was sodium tetrakis[3,5-bis(trifluoromethyl)phenyl]borate (NaBArF) purchased from ABCR GmbH & Co in Karlsruhe, Germany and was used as such to transform the soluble transition metal pyridine-di-imine catalyst precursor to a cationic transition metal catalyst complex, either by separate preparation as described above or by in-situ preparation just prior to addition of an aluminium alkyl or aluminoxane.

The second or solely applied co-catalyst used in the experiments below was selected from:
modified methyl aluminoxane (MMAO) wherein about 25% of the methyl groups are replaced with isobutyl groups. MMAO-3A in heptane ([Al]=6.42% wt), available from AKZO-NOBEL Chemicals B. V., Amersfoort, The Netherlands;
methyl aluminoxane (MAO) in toluene, supplied under the tradename Eurecen AL 5100/10T, batch: B7683; [Al]=4.88% wt, TMA=35.7 wt % (calculated), molecular mass=900 g/mol and [Al]=4.97% wt) supplied by Witco GmbH, Bergkamen, Germany; and
trimethylsilylmethyl lithium, Me$_3$SiCH$_2$Li, 1.0 M solution in pentane from Aldrich.

Examples 15-23

Catalyst System Preparation for (Co)-Oligomerization in a Batch Autoclave

In a Braun MB 200-G dry box the transition metal complex, 2-[1-(2,4,6-trimethylphenylimino)ethyl]-6-[1-(4-eicosanoxy-3,5-diphenylphenylimino)ethyl]pyridine iron [II] chloride complex, 2,6-bis[1-(4-eicosanoxy-3,5-diphenylphenylimino)ethyl]pyridine chromium [III] trichloride or 2,6-bis[1-(4-eicosanoxy-3,5-diphenylphenylimino)ethyl]pyridine iron [II] dichloride (typically about 22.5 μmol) in the presence or absence of an approximately equimolar amount of sodium tetrakis[3,5-bis[trifluoromethyl)phenyl]borate (NaBArF) (see Table 1), was placed in a glass bottle and sealed by a septum. Toluene (typically about 10 ml) was added. Part of these solutions were used in the oligomerization reaction.

Ethylene (Co)-Oligomerizations in a 0.5-litre Batch Autoclave

Oligomerization experiments were performed in a 0.5 litre steel autoclave equipped with jacket cooling with a heating/cooling bath (ex. Julabo, model no. ATS-2) and a turbine/gas stirrer and baffles.

In order to remove traces of water from the reactor, it was evacuated overnight at <10 Pa, and 70° C. The reactor was scavenged by introducing 250 ml toluene, MAO (0.3 g solution) and subsequent stirring at 70° C. under nitrogen pressure of 0.4-0.5 MPa for 30 min. The reactor contents were discharged via a tap in the base of the autoclave. The reactor was evacuated to 0.4 kPa and loaded with approximately 125 ml 1-butene and/or 1-pentene and/or toluene (see Table 1), heated to 40° C. and pressurised with ethylene to the pressure indicated in Table 1.

Whilst stirring, an amount of MAO-solution (see Table 1) was added to the reactor with the aid of toluene (the total volume injected was 12 ml: the MAO-solution diluted with toluene to 4 ml was injected and the injector system was rinsed twice with 4 ml toluene) and the stirring at 800 rpm was continued for 30 minutes.

0.20 μmol of the catalyst system prepared as described above was introduced into the stirred reactor using an injection system with the aid of toluene (the total volume injected was 12 ml: the catalyst solution diluted with toluene to 4 ml was injected and the injector system was rinsed twice with 4 ml toluene). The initial loading of the reactor was about 150 ml alpha-olefin and/or toluene.

The addition of the catalyst system resulted in an exotherm (generally some 5° C.), which generally reached a maximum within 1 minute and was followed by establishment of the temperature and pressure indicated in Table 1.

After consuming the desired volume of ethylene, the oligomerization was stopped by rapid venting of the ethylene, decanting the product mixture into a collection bottle using a tap in the base of the autoclave. Exposure of the mixture to air resulted in rapid deactivation of the catalyst.

After addition of n-hexylbenzene (0.5-3.5 g) as internal standard to the crude product, the amount of the $C_4$-$C_{30}$ olefins and purity of $C_6$, $C_{10}$ and $C_{12}$ olefins was determined by gas chromatography. The Schulz-Flory K-factor and its standard error were determined from the amounts of $C_6$-$C_{28}$ olefins by regression analysis, as described in detail in WO 01/58874. From the Schulz-Flory K-factor the total amount of $C_4$-$C_{100}$ olefins is calculated to compensate for losses in particularly the volatile 1-butene during product isolation. The experimental data is reported in Table 1.

In the case of using chromium catalysts a similarly equipped 1-litre steel autoclave has been used, loaded (similarly to the above-described procedure for the 0.5-litre autoclave) with 300 ml of toluene, a MAO-solution and also n-hexylbenzene (as an internal standard), at the start of the (co)-oligomerization or (co)-polymerization reaction and subsequently maintained at the conditions, decribed in Table 1.

After consuming the desired amount of ethylene the reactor was rapidly cooled to room temperature to minimise evaporation of the volatile products, particularly the butenes. The reaction was stopped by rapid venting of the ethylene and decanting the product mixture into a collection bottle using a tap in the base of the autoclave. Exposure of the mixture to air resulted in rapid deactivation of the catalyst. Since the reactions with ethylene have been carried out in the presence of an internal standard (n-hexylbenzene) and the products have been analysed by the above-described gas chromatographic (GC) method immediately after their isolation, a more reliable amount of the volatile butenes can be established without having to use regression analysis of the higher olefins, a method which can be used in the case of a Schulz-Flory distribution of olefins.

The experimental data is provided in Table 1 below.

TABLE 1

Ethylene (co)-oligomerizations in a 0.5-liter autoclave using soluble 2-[1-(2,4,6-trimethylphenylimino)ethyl]-6-[1-(4-eicosanoxy-3,5-diphenylphenylimino) ethyl]pyridine iron [II] catalyst systems (at 0.20 μmol Fe[II]) or similar soluble transition metal catalyst systems.

| | Co-catalyst | | Process | | Productivity | | | Distribution | | AO Selectivity | | |
|---|---|---|---|---|---|---|---|---|---|---|---|---|
| Example No. | NaBArF | MAO | Conditions | | | Final | TON (TON on | K-factor | | | | |
| (* = comparative example) | μmol (eq) | μmol (eq) | Temp ° C. | Pressure bar(a) | Yield $C_4$ – $C_{100}$ (GC) g | [AO] % wt | Al) mol$C_2^-$/molM | (Standard Error) | | 1 – $C_6^-$ % wt | 1$C_{10}^-$ % wt | 1 – $C_{12}^-$ % wt |
| Example 15* | 0 (0) | 305 (1502) | 70 | 16 | 53.7 | 31.1 | 9.4*E+06 (6300) | 0.67 (0.01) | | 99.5 | 98.4 | 97.8 |
| Example 16 | 0.211 (1.06) | 303 (1515) | 70 | 16 | 52.4 | 30.9 | 9.3*E+06 (6200) | 0.68 (0.01) | | 99.6 | 98.5 | 98.0 |
| Example 17 | 0.201 (1.05) | 195 (970) | 70 | 16 | 18.0 | 12.8 | 3.2*E+06 (3300) | 0.67 (0.01) | | 99.8 | 99.4 | 99.1 |
| Example 18 a) | 0 (0) | 1200 (621) | 70 | 13 | 45.8 (incl. PE = 70 mg) | 16 | 0.90*E+06 | b) | | 30.4 b) | b) | |
| Example 19 a) | 2.12 (1.06) | 1210 (605) | 70 | 16 | 19.9 (incl. PE = 3.3 g) | 7 | 0.36*E+06 | c) | | 50.6 c) | c) | |
| Example 20* just ethene | 0 (0) | (2100) | 50 | 7 | 103.2 | 46 | 12.5*E+06 | 0.73 (0.03) | | 98.8 d) | 96.8 d) | 95.9 d) |
| Example 21 e) | 0 (0) | (2000) | 50 | 7 | Even:80.2 Odd:51.9 | 68 | 12.7*E+06 | Even: 0.68 (0.04) Odd: 0.66 (0.03) | | 97.7 f) 66.0 g) | 92.0 f) g) | 90.6 f) g) |

TABLE 1-continued

Ethylene (co)-oligomerizations in a 0.5-liter autoclave using soluble 2-[1-(2,4,6-trimethylphenylimino)ethyl]-6-[1-(4-eicosanoxy-3,5-diphenylphenylimino) ethyl]pyridine iron [II] catalyst systems (at 0.20 μmol Fe[II]) or similar soluble transition metal catalyst systems.

| Example No. (*= comparative example) | Co-catalyst | | Process Conditions | | Productivity | | | Distribution | AO Selectivity | | |
|---|---|---|---|---|---|---|---|---|---|---|---|
| | NaBArF μmol (eq) | MAO μmol (eq) | Temp °C. | Pressure bar(a) | Yield $C_4$–$C_{100}$ (GC) g | Final [AO] % wt | TON (TON on Al) $molC_2^=/molM$ | K-factor (Standard Error) | $1-C_6^=$ % wt | $1C_{10}^=$ % wt | $1-C_{12}^=$ % wt |
| Example 22 h) | 0 (0) | (2000) | 50 | 7 | 106.8 | 67 | 12.4*E+06 | 0.71 (0.05) | 90.0 i) | 85.0 i) | 85.0 i) |
| Example 23 j) | 0 (0) | (2400) | 50 | 7 | 33.2 | 80 | 3.5*E+06 | 0.15 (0.16) | 39.0 k) | 16.8 k) | n.d. | a) Ethylene oligomerization using 2.0 μmol 2,6-bis[1-(4-eicosanoxy-3,5-diphenylphenylimino) ethyl]pyridine chromium [III] trichloride in 1-liter autoclave, initially loaded with 300 ml toluene, MAO and n-hexylbenzene (ISTD).
b) Largely dimerization: butenes = 92.8% wt (consisting of 1-butene = 97.5, trans 2-butene = 1.5 and cis 2-butene = 1.1% wt); hexenes = 7.0% wt (consisting of 1-hexene = 30.4, 3-methyl-1-pentene = 1.4, 2-ethyl-1-butene = 64.2 and internal hexenes = 3.4% wt), decenes <0.1% wt and polyethylene (PE) <0.2% wt (on total product, including polyethylene).
c) Largely dimerization: butenes = 70.5% wt (consisting of 1-butene = 97.7, trans 2-butene = 1.4 and cis 2-butene 1.0% wt); hexenes = 9.0% wt (consisting of 1-hexene = 50.6, 3-methyl-1-pentene = 0.9, 2-ethyl-1-butene = 46.0 and internal hexenes = 2.6% wt), decenes = 1.1% wt and polyethylene (PE) = 16.4% wt (on total product, including polyethylene).
d) Hexenes: 1-hexene = 98.8, 3-methyl-1-pentene = 0.9, 2-ethyl-1-butene = 0.1 and internal hexenes = 0.2% wt; branched $C_{10}$ = 2.9, internal $C_{10}$ = 0.3, branched $C_{12}$ = 3.9 and internal $C_{12}$ = 0.1% wt.
e) Co-oligomerization of 1-pentene and ethylene using 150 ml of 1-pentene/toluene in a ratio of 1.04 v/v, instead of toluene and 30 μmol 2-[1-(2,4,6-trimethylphenylimino) ethyl]-6-[1-(4-eicosanoxy-3,5-diphenylphenylimino)ethyl]pyridine iron [II] dichloride.
f) Hexenes: 1-hexene = 97.7, 3-methyl-1-pentene = 1.6, 2-ethyl-1-butene = 0.2 and internal hexenes = 0.4% wt; branched $C_{10}$ = 6.8, internal $C_{10}$ = 1.3, branched $C_{12}$ = 8.5 and internal $C_{12}$ = 0.9% wt.
g) Heptenes: 1-heptene = 66.0, 3-methyl-1-hexene = 29.2 and 2-ethyl-1-pentene = 3.8, internal heptenes = 1.1% wt; 1-nonene = 56.8, 1-undecene = 61.6 and 1-tridecene = 58.8% wt.
h) Co-oligomerization of 1-butene and ethylene using 150 ml of 1-butene/toluene in a ratio of 0.79 v/v, instead of toluene and 30 μmol 2-[1-(2,4,6-trimethylphenylimino) ethyl]-6-[1-(4-eicosanoxy-3,5-diphenylphenylimino)ethyl]pyridine iron [II] dichloride.
i) Hexenes: 1-hexene = 90.0, 3-methyl-1-pentene = 8.3, 2-ethyl-1-butene = 0.2 and internal hexenes = 1.3% wt; branched $C_{10}$ = 12.8, internal $C_{10}$ = 2.2, branched $C_{12}$ = 14.1 and internal $C_{12}$ = 0.9% wt.
j) Co-oligomerization of 1-butene and ethylene using 150 ml of 1-butene/toluene in a ratio of 6.67 v/v, instead of toluene and 34 μmol 2,6-bis[1-(4-eicosanoxy-3,5-diphenylphenylimino) ethyl]pyridine iron [II] dichloride.
k) Hexenes: 1-hexene = 39.0, 3-methyl-1-pentene = 3.3, 2-ethyl-1-butene = 36.2 and internal hexenes = 19.0% wt; branched $C_{10}$ = 77.0 and internal $C_{10}$ = 6.2% wt.

Upon replacing a minute quantity (approximately 1.05 equivalents based on moles of transition metal, or about 0.21 μmol) of the MAO co-catalyst (generally present in about 300 μmol) with a transition metal complex cation generating compound, such as sodium tetrakis[3,5-bis[trifluoromethyl)phenyl]borate (NaBArF), the selectivity towards linear alpha olefins (as measured by the % wt $1-C_6^=$, $1-C_{10}^=$ and $1-C_{12}^=$ of the respective $C_6$, $C_{10}$ and $C_{12}$ fractions) is at least on a par with the experiments performed in the absence of NaBArF (see examples 15-17).

On addition of NaBArF, the selectivity towards linear alpha olefins based upon the total olefin yield remains at least on a par with that of the experiments without NaBArF addition, as is clear from the yield of $C_4$-$C_{100}$ oligomers and the turnover number (TON=the amount of moles of ethylene converted per mol of Fe) (see examples 15 and 16).

The Schulz-Flory K-factor and its standard error remain the same for the experiments performed both in the presence and the absence of NaBArF. The standard error, which is a measure for deviation from a genuine Schulz-Flory distribution, described in WO 01/58874, is very low, indicating that no tail of heavy olefins ($C_{30}$-$C_{100}$) are being formed in either case.

It can also be seen that use of a reduced amount of MAO co-catalyst with NaBArF does not detrimentally affect the selectivity of the catalyst towards linear alpha-olefins (see examples 15-17).

Another advantage of the soluble transition metal catalyst precursors is that by using transition metal complex cation generating compounds, such as NaBArF, alternative compounds capable of transferring a hydrocarbyl or hydride group to MAO or MMAO can be employed easily, such as any suitable compounds known to those skilled in the art, for example RLi, $R_2Zn$ or $R_3Al$.

The ethylene oligomerization and/or polymerization, using soluble Cr[III] catalysts in the presence or absence of NaBArF are also summarised in Table 1 (examples 18 and 19). It is noted that in the absence of NaBArF the soluble chromium complex gives rise to largely dimer formation (1-butene>90% wt of the total product) at a turnover number (TON) about one order of magnitude lower than for similar Fe[II] catalysts. The 1-hexene content of the hexenes is low (30.4% wt); the predominant product being 2-ethyl-1-butene. A small amount (70 mg) of polyethylene (PE) is formed as well (in two repeat experiments the amounts of PE were 31 and 91 mg, respectively, whereas the relative amount of dimers remained constant).

In the presence of 1 equivalent of NaBArF the same Cr[III] complex also gave largely dimer formation (1-butene is 69% wt of the total product) at a somewhat lower TON. The 1-hexene content of the hexenes was higher (50.6% wt); a large by-product also being 2-ethyl-1-butene. Furthermore, a large amount (3.3 g; 16.4% wt) of high molecular weight polyethylene (PE) is formed. Differential Scanning Calorimetry (DSC) of the PE showed a melting point of 127° C. Upon repeat of the experiment the product contained less (12.4% wt) high molecular weight polymer (DSC m.p.=129° C.).

The co-oligomerization of alpha-olefins, such as 1-pentene and 1-butene, and ethylene, using soluble Fe[II] catalysts in the presence or absence of NaBArF are summarised in Table 1 (examples 20-23). In example 21, 39% wt of the product consists of odd-numbered olefins, which indicates that 1-pentene is co-oligomerised under the conditions employed.

Upon the use of the symmetrical soluble Fe[II] catalyst K (Example 23), a catalyst with a low k-factor (low propagation) the product spectrum was surprisingly different from that of catalyst E. Contrary to the catalyst systems comprising iron complex E, when catalyst systems comprising the symmetrical iron complex K are used, a relatively large amount of 1-butene undergoes 1,2-insertion into iron-ethyl, believed to be leading to 2-ethyl-1-butene formation.

Examples 24-31

Catalyst System Preparation for Dimerization in a Batch Autoclave

In a Braun MB 200-G dry box, the 2-[1-(2,4,6-trimethylphenylimino)ethyl]-6-[1-(4-eicosanoxy-3,5-diphenylphenylimino)ethyl]pyridine cobalt[II] chloride tetrakis[3,5-bis[trifluoromethyl)phenyl]borate, the 2-[1-(2,4,6-trimethylphenylimino)ethyl]-6-[1-(4-eicosanoxy-3,5-diphenylphenylimino)ethyl]pyridine cobalt[II] dichloride complex or the 2-[1-(2-tert-butylphenylimino)ethyl]-6-[1-(4-eicosanoxy-3,5-diphenylphenylimino)ethyl]pyridine cobalt[II] dichloride complex, in the presence or absence of an approximately equimolar amount of sodium tetrakis[3,5-bis[trifluoromethyl)phenyl]borate (NaBArF) (typically about 50 μmol—see Table 2), was placed in a glass bottle sealed by a septum. Toluene (typically about 10 ml) was added. The resulting mixture was stirred for at least a half of hour. Part of these solutions were used in the dimerization experiments below.

Alpha-Olefin Dimerizations in a 0.5-litre Batch Autoclave

The dimerization experiments were performed in a 0.5 litre steel autoclave equipped with jacket cooling with a heating/cooling bath (ex. Julabo, model no. ATS-2) and a turbine/gas stirrer and baffles.

In order to avoid traces of water, the reactor was kept under nitrogen pressure (0.5 MPa) at room temperature. Prior the experiment the reactor was scavenged by introducing 250 ml toluene, MAO (0.3 g solution) and subsequent stirring at 70° C. under nitrogen pressure of 0.5-0.6 MPa for 30 min. The reactor contents were discharged via a tap in the base of the autoclave. The reactor was evacuated to 0.4 kPa and cooled to 20° C. After which it was loaded with 120 ml 1-butene (grade 2.0, Hoek Loos) and the reactor was heated to 30° C.

Under stirring, the MAO-solution (minimum 210 mg) was then added to the reactor with the aid of toluene (the MAO-solution was injected, the injector was subsequently rinsed twice, bringing the total volume injected was 10 ml) and the stirring at 800 rpm was continued for 60 minutes.

The required amount (50 μmol) of the catalyst solution, preparation of which is described above, was introduced into the stirred reactor using an injection system, after that the injector was rinsed three times with 3-4 ml toluene (total contents of reactor 150 ml).

The addition of the catalyst system resulted in a small exotherm (generally 3-8° C.), which was easily absorbed by the thermostat bath, bringing the reactor back to the initial conditions.

After about 2 hours, the experiment was stopped by decanting the product mixture into a collection bottle using a tap in the base of the autoclave. Exposure of the mixture to air resulted in rapid deactivation of the catalyst.

After addition of n-hexylbenzene (0.5-3.5 g), as internal standard, to the crude product, the amount and purity of $C_4$, $C_8$ and $C_{12}$ olefins was determined by gas chromatography.

The results of the alpha olefin, mainly 1-butene, dimerization experiments are given in Table 2 and in the detailed descriptions below.

On one occasion 1-pentene was used in a small-scale dimerization experiment at ambient temperature and pressure in a nitrogen atmosphere in a stirred vessel in the dry box (see Table 2, example 30 and the detailed description of the Example 30). Activation (by alkylation) of the cationic cobalt complex, can also be achieved in-situ by stepwise activation of the cobalt cationic complex by 1 equivalent of NaBArF, followed by addition of 1 equivalent of trimethylsilylmethyl lithium, Me$_3$SiCH$_2$Li, instead of MAO or MMAO. This demonstrates that the catalyst can be activated without MAO or MMAO.

Example 30 (see Table 2)

Reaction of 1-pentene Catalysed by an Activated Cationic Co[II] Complex G

In an inert atmosphere (in dry box) in a stirred vessel at ambient temperature, 1-pentene (4.6 g; 65.7 mmol) was dimerised to a mixture of linear cis and trans 3-decene and 4-decene (2.8% wt 2-propyl-1-heptene is the main branched impurity), using 11.3 μmol cationic Co[II] catalyst, 2-[1-(2,4,6-trimethylphenylimino)ethyl]-6-[1-(4-eicosanoxy-3,5-diphenylphenylimino)ethyl]pyridine cobalt[II] chloride tetrakis[3,5-bis[trifluoromethyl)phenyl]borate, activated by addition of 1 equivalent of Me$_3$SiCH$_2$Li (alkylation), instead of MAO. 1-Pentene was converted to linear cis/trans 3-decenes and 4-decenes (2.8% wt 2-propyl-1-heptene is the main branched impurity) and cis/trans 2-pentene in about equal amounts. The results are summarised in Table 2.

The products were analysed by GC and NMR and the results are given in Table 2.

TABLE 2

Alpha olefin dimerization experiments in 0.5-liter autoclave using soluble 2-[1-(2,4,6-trimethylphenylimino)ethyl]-6-[1-(4-eicosanoxy-3,5-diphenylphenylimino)ethyl] pyridine cobalt[II] catalyst systems (at 50 μmol cobalt[II]) or similar soluble transition metal catalyst systems.

| Example | Co-catalyst | | Process Conditions | | Productivity | | |
|---|---|---|---|---|---|---|---|
| No. (* = comparative example) | NaBArF μmol (eq) | (M)MAO μmol (eq) | Temp ° C. | Press bar (a) | Yield $C_8$-$C_{32}$ (GC) g | Conversion of $C_4^=$ to $C_8^=$ % | $\dfrac{\text{TON(Co) 2*mol } C_8^=}{\text{mol Co}}$ |
| Example 24* (Lit) a) | 0 | ~6500 (~600) | 30 | — | 26.0 | 19 | 36000 |

TABLE 2-continued

Alpha olefin dimerization experiments in 0.5-liter autoclave using soluble 2-[1-(2,4,6-trimethylphenylimino)ethyl]-6-[1-(4-eicosanoxy-3,5-diphenylphenylimino)ethyl] pyridine cobalt[II] catalyst systems (at 50 μmol cobalt[II]) or similar soluble transition metal catalyst systems.

| Example | | | | | | | |
|---|---|---|---|---|---|---|---|
| Example 25* (Lit) b) | 0 | 10600 (500) | 30 | — | 153 | 50.2 | 10500 |
| Example 26* (Lit) c) | 0 | 26500 (500) | 30 | — | 96.7 | 39 | 32000 |
| Example 27* d) | 0 | 25018 (502) | 30 | 3.0 | 15.1 | 22.4 | 5300 |
| Example 28 | 48.8 (1.00) | 487 (10) | 30 | 3.4 | 19.5 | 29.0 | 7100 |
| Example 29 | 53.0 (1.04) | 1205 (24) | 30 | 3.0 | 25.7 | 38.2 | 9000 |
| Example 30 e) | 11.3 (1.0) | e) | 20 | 1 | 1.2 e) | 26 e) | 1500 e) |
| Example 31 f) | 48.0 (1.04) | 1146 (24) | 30 | 3.0 | 12.0 | 17.8 | 4400 |

| Example | | Selectivity | | |
|---|---|---|---|---|
| No. (* = comparative example) | $\dfrac{\text{TON(Al) } 2^* \text{mol } C_8^=}{\text{mol Al}}$ | $\dfrac{\text{Total} - C_8}{(C_8-C_{32})} \% \text{ wt}$ | Linear $2 + 3 - C_8^=$ on all $C_8^=$, % wt | $\dfrac{2 + 3 - C_8^= \text{ (Dimers)}}{2 - C_4^= \text{ (Isomers)}} \text{ g/g}$ |
| Example 24* (Lit) a) | <50 | 85 | 71 | — |
| Example 25* (Lit) b) | 200 | 82 | 70 | >20 b) |
| Example 26* (Lit) c) | 65 | 99 | 97 | 0.70 |
| Example 27* d) | 11 | 99 | 92 | 0.46 |
| Example 28 | 710 | >99 | 97 | 0.96 |
| Example 29 | 380 | >99 | 96 | 0.97 |
| Example 30 e) | 1500 e) | >99 e) | 97 e) | e) |
| Example 31 f) | 185 | 99 | 98 | 3.24 | a) Using 10.9 μmol 2,6-bis[1-(2-methylphenylimino)ethyl]pyridine iron[II] chloride complex and MMAO according to B. L. Small, E. J Baralt, A. J. Marcucci, U.S. Pat. No. 6,291,733 B1 of 18$^{th}$ September 2001.

b) Using 21.2 μmol 2,6-bis[1-(2-methylphenylimino)ethyl]pyridine iron[II] chloride complex and MMAO according to B. L. Small, Organometallics 2003, 22, 3178-3183; in this case the dimer/isomer ratio is replaced by the oligomer/isomer ratio.

c) Using 53.1 μmol 2,6-bis[1-(2-methylphenylimino)ethyl]pyridine cobalt[II] chloride complex and MMAO according to B. L. Small, Organometallics 2003, 22, 3178-3183.

d) In a preceeding experiment it was observed that stepwise addition of MAO (1200-16000 μmol), followed by an additional 17 μmol soluble Co[II] catalyst precursor did not initiate dimerization; dimerization only started after addition to this system of 4.6 μmol of the cationic Co[II] catalyst system, 2-[1-(2,4,6-trimethylphenylimino)ethyl]-6-[1-(4-eicosanoxy-3,5-diphenylphenylimino) ethyl]pyridine cobalt[II] chloride tetrakis[3,5-bis[trifluoromethyl)phenyl] borate.

e) On a small scale, using 1-pentene and 2-[1-(2,4,6-trimethylphenylimino)ethyl]-6-[1-(4-eicosanoxy-3,5-diphenylphenylimino) ethyl]pyridine cobalt[II] chloride tetrakis[3,5-bis[trifluoromethyl)phenyl] borate (cationic Co[II] complex), activated by addition of 1 equivalent of $Me_3SiCH_2Li$ (alkylation), instead of MAO. 1-Pentene was converted to linear cis/trans 3- and 4-decenes (2.8% wt 2-propyl-1-heptene is the main branched impurity) and cis/trans 2-pentene in about equal amounts.

f) Using 48 μmol of the alternate toluene-soluble Co[II] catalyst system, derived from the 2-[1-(2-tert-butylphenylimino)ethyl]-6-[1-(4-eicosanoxy-3,5-diphenylphenylimino) ethyl]pyridine cobalt[II] dichloride complex, (0).

From these examples it is clear that upon the use of soluble cationic transition metal complexes, which are formed by stepwise activation of the neutral transition metal complex by addition of a stoichiometric amount of NaBArF, subsequently followed by activation with a relatively small amount of MAO or MMAO, a higher TON on aluminium (MAO) is obtained in comparison to a transition metal complex activated MAO or MMAO alone (see Examples 26 and 28). The soluble Co[II] catalysts have a selectivity to dimers relative to higher oligomers, which is on a par with the non-soluble catalysts described in the literature (see Table 2, Example 29 and comparative Example 26). The same is true for the head-to-head dimerization selectivity, which affords linear dimers. It is noted that selectivities towards linear dimer formation are much higher for Co[II] catalysts than for Fe[II].

We have surprisingly found that the use of a soluble cobalt [II] cationic catalyst, either prepared seperately or prepared in-situ, enhances the selectivity towards dimers over that of double bond shift (isomerisation), in comparison with the Co[II] catalysts activated by addition of a large excess of MMAO as described in the literature (see Table 2, examples 26, 28 and 29).

Use of the soluble catalyst system derived from 2-[1-(2-tert-butylphenylimino)ethyl]-6-[1-(4-eicosanoxy-3,5-diphenylphenylimino)ethyl]pyridine cobalt [II] dichloride complex (O) by in-situ addition of 1 equivalent of NaBArF (Table 2, example 31), results in a significantly higher selectivity towards linear dimer formation (less isomerisation of 1-butene to 2-butenes) compared to the Co[II] catalyst of Example 26, which is described in the literature.

We claim:

1. A transition metal complex which is soluble in non-polar media and is a bis-arylimine pyridine $MX_n$ complex, comprising a bis-arylimine pyridine ligand having the formula (I) below:

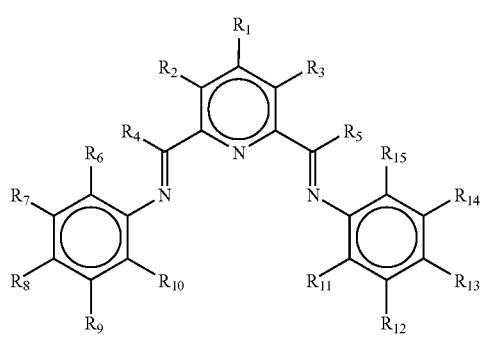

(I)

wherein any two of $R_1$-$R_3$ form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed, and the one of $R_1$-$R_3$ that is not part of a ring and $R_4$-$R_5$, $R_7$-$R_9$, $R_{12}$ and $R_{14}$ are each, independently, hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or any two of $R_7$-$R_9$ vicinal to one another taken together may form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed; and $R_6$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_7$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{10}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_9$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{11}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{12}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{15}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{14}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; provided that $R_{13}$ and at least one of $R_{12}$ and $R_{14}$ are independently selected from optionally substituted $C_1$-$C_{20}$ alkyl, optionally substituted $C_4$-$C_{20}$ alkyloxy, halogen and optionally substituted $C_5$-$C_{20}$ aryl, or $R_{13}$ taken together with $R_{12}$ or $R_{14}$ form a ring which is an optionally substituted $C_5$-$C_{20}$ cyclic hydrocarbyl group optionally substituted with only carbon and hydrogen atoms and optionally containing one or more heteroatom-containing functional groups that do not interfere to any substantial degree with the catalytic process in which said complex may be employed, and provided that at least one of $R_{12}$, $R_{13}$ and $R_{14}$ is optionally substituted $C_4$-$C_{20}$ alkyloxy;

M is a transition metal atom selected from Ti, V, Cr, Mn, Ni, Pd, Rh, Ru, Mo, Nb, Zr, Hf, Ta, W, Re, Os, Ir or Pt;

n matches the formal oxidation state of the transition metal atom M; and

X is halide, optionally substituted hydrocarbyl, alkoxide, amide, or hydride.

2. A transition metal complex according to claim 1 wherein $R_{12}$, $R_{13}$ and $R_{14}$ are all independently selected from optionally substituted $C_1$-$C_{20}$ alkyl, optionally substituted $C_4$-$C_{20}$ alkyloxy and optionally substituted $C_5$-$C_{20}$ aryl with the proviso that at least one of $R_{12}$, $R_{13}$ and $R_{14}$ is optionally substituted $C_4$-$C_{20}$ alkyloxy.

3. A transition metal complex according to claim 1 wherein $R_{13}$ and at least one of $R_{12}$ and $R_{14}$ are independently selected from optionally substituted $C_3$-$C_{20}$ alkyl, optionally substituted $C_4$-$C_{20}$ alkyloxy and optionally substituted $C_5$-$C_6$ aryl with the proviso that at least one of $R_{12}$, $R_{13}$ and $R_{14}$ is optionally substituted $C_4$-$C_{20}$ alkyloxy.

4. A transition metal complex according to claim 1 wherein $R_8$ and at least one of $R_7$ and $R_9$ are said hydrocarbyl and are independently selected from optionally substituted $C_1$-$C_{20}$ alkyl, optionally substituted $C_4$-$C_{20}$ alkyloxy, halogen and optionally substituted $C_5$-$C_{20}$ aryl, or $R_8$ taken together with $R_7$ or $R_9$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, or $R_7$ taken together with $R_6$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed and $R_9$ taken together with $R_{10}$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, with the proviso that at least one of $R_7$, $R_8$ and $R_9$ is optionally substituted $C_4$-$C_{20}$ alkyloxy.

5. A transition metal complex according to claim 4, wherein $R_8$ and at least one of $R_7$ and $R_9$ are said hydrocarbyl and are independently selected from optionally substituted $C_3$-$C_{20}$ alkyl, optionally substituted $C_4$-$C_{20}$ alkyloxy and optionally substituted $C_5$-$C_6$ aryl with the proviso that at least one of $R_7$, $R_8$ and $R_9$ is optionally substituted $C_4$-$C_{20}$ alkyloxy.

6. A transition metal complex according to claim 1 wherein $R_7$, $R_8$ and $R_9$ are said hydrocarbyl and are all independently selected from optionally substituted $C_1$-$C_{20}$ alkyl, optionally substituted $C_4$-$C_{20}$ alkyloxy and optionally substituted $C_5$-$C_{20}$ aryl with the proviso that at least one of $R_7$, $R_8$ and $R_9$ is optionally substituted $C_4$-$C_{20}$ alkyloxy.

7. A transition metal complex according to claim 1 wherein said optionally substituted $C_4$-$C_{20}$ alkyloxy group is an eicosanoxy group.

8. A transition metal complex which is soluble in non-polar media and is a [bis-arylimine pyridine $MX_p^+$][$NC^-$]$_q$ complex, comprising a bis-arylimine pyridine ligand having the formula (I) below:

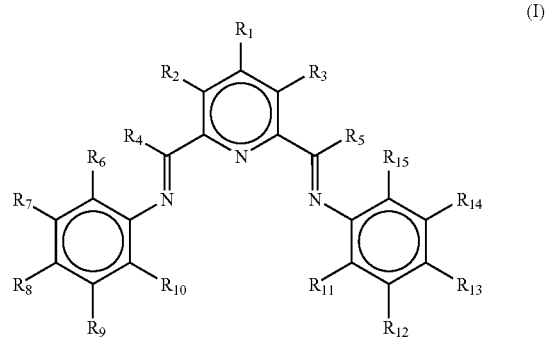

(I)

wherein any two of $R_1$-$R_3$ form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed, and the one of $R_1$-$R_3$ that is not part of a ring and $R_4$-$R_5$, $R_7$-$R_9$, $R_{12}$ and $R_{14}$ are each, independently, hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or any two of $R_7$-$R_9$ vicinal to one another taken together may form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed; and $R_6$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_7$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed;

$R_{10}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_9$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{11}$ is hydrogen, a hydrocarbyl containing only 1 to 20 carbon and hydrogen atoms and optionally containing one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{12}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{15}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{14}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; provided that $R_{13}$ and at least one of $R_{12}$ and $R_{14}$ are independently selected from optionally substituted $C_1$-$C_{20}$ alkyl, optionally substituted $C_4$-$C_{20}$ alkyloxy, halogen and optionally substituted $C_5$-$C_{20}$ aryl, or $R_{13}$ taken together with $R_{12}$ or $R_{14}$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, and provided that at least one of $R_{12}$, $R_{13}$ and $R_{14}$ is optionally substituted $C_4$-$C_{20}$ alkyloxy;

M is a transition metal atom selected from Ti, V, Cr, Mn, Ni, Pd, Rh, Ru, Mo, Nb, Zr, Hf, Ta, W, Re, Os, Ir or Pt;

X is halide, optionally substituted hydrocarbyl, alkoxide, amide, or hydride; $NC^-$ is a non-coordinating anion; and p+q matches the formal oxidation state of the transition metal atom M.

9. A transition metal complex according to claim 8, wherein $R_{12}$, $R_{13}$ and $R_{14}$ are all independently selected from optionally substituted $C_1$-$C_{20}$ alkyl, optionally substituted $C_4$-$C_{20}$ alkyloxy and optionally substituted $C_5$-$C_{20}$ aryl with the proviso that at least one of $R_{12}$, $R_{13}$ and $R_{14}$ is optionally substituted $C_4$-$C_{20}$ alkyloxy.

10. A transition metal complex according to claim 8, wherein $R_{13}$ and at least one of $R_{12}$ and $R_{14}$ are independently selected from optionally substituted $C_3$-$C_{20}$ alkyl, optionally substituted $C_4$-$C_{20}$ alkyloxy and optionally substituted $C_5$-$C_6$ aryl with the proviso that at least one of $R_{12}$, $R_{13}$ and $R_{14}$ is optionally substituted $C_4$-$C_{20}$ alkyloxy.

11. A transition metal complex according to claim 8 wherein $R_8$ and at least one of $R_7$ and $R_9$ are said hydrocarbyl and are independently selected from optionally substituted $C_1$-$C_{20}$ alkyl, optionally substituted $C_4$-$C_{20}$ alkyloxy, halogen and optionally substituted $C_5$-$C_{20}$ aryl, or $R_8$ taken together with $R_7$ or $R_9$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, or $R_7$ taken together with $R_6$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed and $R_9$ taken together with $R_{10}$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, with the proviso that at least one of $R_7$, $R_8$ and $R_9$ is optionally substituted $C_4$-$C_{20}$ alkyloxy.

12. A transition metal complex according to claim 11 wherein $R_8$ and at least one of $R_7$ and $R_9$ are said hydrocarbyl and are independently selected from optionally substituted $C_3$-$C_{20}$ alkyl, optionally substituted $C_4$-$C_{20}$ alkyloxy and optionally substituted $C_5$-$C_6$ aryl with the proviso that at least one of $R_7$, $R_8$ and $R_9$ is optionally substituted $C_4$-$C_{20}$ alkyloxy.

13. A transition metal complex according to claim 8 wherein $R_7$, $R_8$ and $R_9$ are said hydrocarbyl and are all independently selected from optionally substituted $C_1$-$C_{20}$ alkyl, optionally substituted $C_4$-$C_{20}$ alkyloxy and optionally substituted $C_5$-$C_{20}$ aryl with the proviso that at least one of $R_7$, $R_8$ and $R_9$ is optionally substituted $C_4$-$C_{20}$ alkyloxy.

14. A transition metal complex according to claim 8 wherein said optionally substituted $C_4$-$C_{20}$ alkyloxy group is an eicosanoxy group.

15. A bis-arylamine pyridine ligand having the formula (I) below:

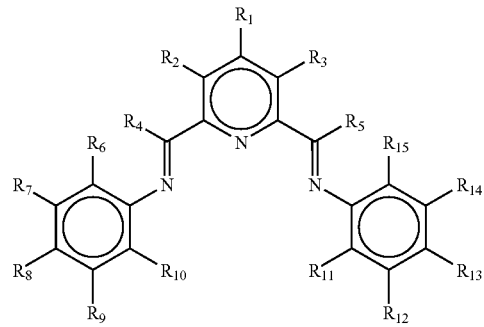

(I)

wherein any two of $R_1$-$R_3$ form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed, and the one of $R_1$-$R_3$ that is not part of a ring and $R_4$-$R_5$, $R_7$-$R_9$, $R_{12}$ and $R_{14}$ are each, independently, hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or any two of $R_7$-$R_9$ vicinal to one another taken together may form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed; and $R_6$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_7$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{10}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_9$ to form a ring which is an optionally substituted $C_5$-$C_{20}$ cyclic hydrocarbyl group optionally substituted with only carbon and hydrogen atoms and optionally containing one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{11}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{12}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{15}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{14}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; provided that $R_{13}$ and at least one of $R_{12}$ and $R_{14}$ are independently selected from optionally substituted $C_1$-$C_{20}$ alkyl, optionally substituted $C_4$-$C_{20}$ alkyloxy, halogen and optionally substituted $C_5$-$C_{20}$ aryl, or $R_{13}$ taken together with $R_{12}$ or $R_{14}$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, and provided that at least one of $R_{12}$, $R_{13}$ and $R_{14}$ is optionally substituted $C_4$-$C_{20}$ alkyloxy.

16. A bis-aryliminio pyridine ligand according to claim 15 wherein $R_8$ and at least one of $R_7$ and $R_9$ are said hydrocarbyl and are independently selected from optionally substituted $C_1$-$C_{20}$ alkyl, optionally substituted $C_4$-$C_{20}$ alkyloxy, halogen and optionally substituted $C_5$-$C_{20}$ aryl, or $R_8$ taken together with $R_7$ or $R_9$ form a ring which is a $C_5$-$C_{20}$ cyclic hydrocarbyl group containing only carbon and hydrogen atoms and optionally containing one or more heteroatom-containing functional groups that do not interfere to any substantial degree with the catalytic process in which said complex may be employed, or $R_7$ taken together with $R_6$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed and $R_9$ taken together with $R_{10}$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, with the proviso that at least one of $R_7$, $R_8$ and $R_9$ is optionally substituted $C_4$-$C_{20}$ alkyloxy.

17. A transition metal complex according to claim 1 wherein M is a transition metal selected from Fe and Co and wherein the transition metal complex is not 2-[1-(2,4,6-trimethylphenylimino) ethyl]-6-[1-(4-eicosanoxy-3,5-diphenylphenylimino)ethyl]pyridine iron (II) chloride complex.

18. A transition metal complex according to claim 17 wherein $R_8$ and at least one of $R_7$ and $R_9$ are said hydrocarbyl and are independently selected from optionally substituted $C_3$-$C_{20}$ alkyl, optionally substituted $C_4$-$C_{20}$ alkyloxy and optionally substituted $C_5$-$C_6$ aryl with the proviso that at least one of $R_7$, $R_8$ and $R_9$ is optionally substituted $C_4$-$C_{20}$ alkyloxy.

19. A transition metal complex according to claim 8 wherein M is a transition metal selected from Fe and Co.

20. A transition metal complex according to claim 19 wherein $R_8$ and at least one of $R_7$ and $R_9$ are said hydrocarbyl and are independently selected from optionally substituted $C_3$-$C_{20}$ alkyl, optionally substituted $C_4$-$C_{20}$ alkyloxy and optionally substituted $C_5$-$C_6$ aryl with the proviso that at least one of $R_7$, $R_8$ and $R_9$ is optionally substituted $C_4$-$C_{20}$ alkyloxy.

21. A catalyst system comprising:
  (a) one or more transition metal complexes which are soluble in non-polar media and are a bis-arylimine pyridine $MX_n$ complex or a [bis-arylimine pyridine $MX_p^+$][$NC^{31}$]$_q$ complex, each comprising a bis-arylimine pyridine ligand of formula (I) below:

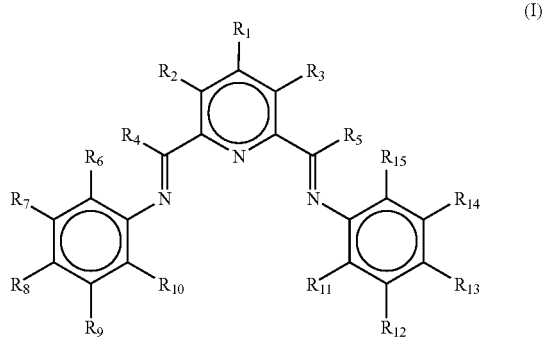

wherein any two of $R_1$-$R_3$ form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed, and the one of $R_1$-$R_3$ that is not part of a ring and $R_4$-$R_5$, $R_7$-$R_9$, $R_{12}$ and $R_{14}$ are each, independently, hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or any two of $R_7$-$R_9$ vicinal to one another taken together may form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed; and $R_6$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_7$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{10}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_9$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{11}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{12}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{15}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{14}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; provided that $R_{13}$ and at least one of $R_{12}$ and $R_{14}$ are independently selected from optionally substituted $C_1$-$C_{20}$ alkyl, optionally substituted $C_4$-$C_{20}$ alkyloxy, halogen and optionally substituted $C_5$-$C_{20}$ aryl, or $R_{13}$ taken together with $R_{12}$ or $R_{14}$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, and provided that at least one of $R_{12}$, $R_{13}$ and $R_{14}$ is optionally substituted $C_4$-$C_{20}$ alkyloxy;

M is a transition metal atom;

n matches the formal oxidation state of the transition metal atom M;

X is halide, optionally substituted hydrocarbyl, alkoxide, amide, or hydride;

NC⁻ is a non-coordinating anion; and p+q matches the formal oxidation state of the transition metal atom M; and mixtures thereof; and (b)(i) in the case when a bis-arylimine pyridine $MX_n$ complex is present, (1) a co-catalyst compound capable of abstracting an anion and transferring a hydrocarbyl or hydride group to the transition metal atom, or (2) a co-catalyst compound capable of abstracting an anion and a co-catalyst compound capable of transferring a hydrocarbyl or hydride group to the transition metal atom; and/or (b)(ii) in the case where a [bis-arylimine pyridine $MX_p^+$] [$NC^-$]$_q$ complex is present, a co-catalyst compound capable of transferring a hydrocarbyl or hydride group to the transition metal atom.

22. A catalyst system according to claim 21 wherein M is a transition metal selected from Fe and Co with the proviso that the catalyst system does not comprise one or more compounds of the formula $ZnR'_2$ wherein each R', which may be the same or different, is selected from hydrogen, optionally substituted $C_1$-$C_{20}$ hydrocarbyl, phenyl, Cl, Br, I, SR", $NR''_2$, OH, OR", CN, NC wherein R", which within the same molecule may the same or different, is $C_1$-$C_{20}$ hydrocarbyl, and the catalyst system is not 2-[1-(2,4,6-trimethylphenylimino) ethyl]-6-[1-(4-eicosanoxy-3,5-diphenylphenylimino)ethyl] pyridine iron[II] chloride complex with MAO, or with the proviso that when the transition metal is Fe, the catalyst system is not 2-[1-(2,4,6-trimethylphenylimino) ethyl]-6-[1-(4-eicosanoxy-3,5-diphenylphenylimino)ethyl] pyridine iron [II] chloride complex with MAO or 2-[1-(2,4,6-trimethylphenylimino) ethyl]-6-[1-(4-eicosanoxy-3,5-diphenylphenylimino)ethyl] pyridine iron[II] chloride complex with MAO and $ZnEt_2$.

23. A continuous dimerization or co-oligomerization process comprising contacting a feed olefin in non-polar media, which is an alpha-olefin comprising at least 3 carbon atoms or an alpha olefin comprising 3 carbon atoms and ethylene, with a catalyst system comprising:

(a) one or more transition metal complexes which are soluble in non-polar media and are selected from the group consisting of a transition metal complex which is a bis-arylimine pyridine MXn complex and a [bis-arylimine pyridine MXp+][NC−]q complex, each comprising a bis-arylimine pyridine ligand having the formula (I)

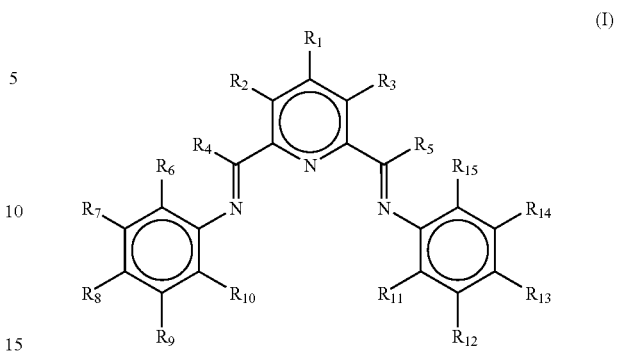

wherein any two of $R_1$-$R_3$ form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed, and the one of $R_1$-$R_3$ that is not part of a ring and $R_4$-$R_5$, $R_7$-$R_9$, $R_{12}$ and $R_{14}$ are each, independently, hydrogen, a hydrocarbyl containing 1 to 20 carbon and hydrogen atoms and optionally substituted with one or more heteroatom-containing functional groups that do not interfere to any substantial degree with the catalytic process in which said complex may be employed a functional group other than said hydrocarbyl group which does not interfere to any substantial degree with the catalytic process in which said complex may be employed, or any two of $R_7$-$R_9$ vicinal to one another taken together may form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed; and $R_6$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_7$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{10}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_9$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{11}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{12}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{15}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{14}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; provided that $R_{13}$ and at least one of $R_{12}$ and $R_{14}$ are independently selected from optionally substituted $C_1$-$C_{20}$ alkyl, optionally substituted $C_4$-$C_{20}$ alkyloxy, halogen and optionally substituted $C_5$-$C_{20}$ aryl, or $R_{13}$ taken together with $R_{12}$ or $R_{14}$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, and provided that at least one of $R_{12}$, $R_{13}$ and $R_{14}$ is optionally substituted $C_4$-$C_{20}$ alkyloxy;

M is a transition metal atom;

n matches the formal oxidation state of the transition metal atom M;

X is halide, optionally substituted hydrocarbyl, alkoxide, amide, or hydride;

$NC^-$ is a non-coordinating anion; and p+q matches the formal oxidation state of the transition metal atom M;

(b)(i) in the case when a bis-arylimine pyridine $MX_n$ complex is present, (1) a co-catalyst compound capable of abstracting an anion and transferring a hydrocarbyl or hydride group to the transition metal atom, or (2) a co-catalyst compound capable of abstracting an anion and a co-catalyst compound capable of transferring a hydrocarbyl or hydride group to the transition metal atom; and/or (b)(ii) in the case where a [bis-arylimine pyridine $MX_p^+$] $[NC^-]_q$ complex is present, a co-catalyst compound capable of transferring a hydrocarbyl or hydride group to the transition metal atom.

24. A continuous oligomerization process comprising contacting ethylene in non-polar media with a catalyst system comprising:

(a) one or more transition metal complexes which are soluble in non-polar media and are selected from the group consisting of a transition metal complex which is a bis-arylimine pyridine MXn complex and a [bis-arylimine pyridine MXp+][NC−]q complex, each comprising a bis-arylimine pyridine ligand having the formula (I)

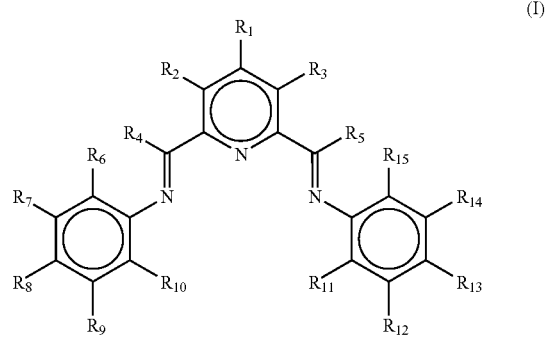

wherein any two of $R_1$-$R_3$ form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed, and the one of $R_1$-$R_3$ that is not part of a ring and $R_4$-$R_5$, $R_7$-$R_9$, $R_{12}$ and $R_{14}$ are each, independently, hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or any two of $R_7$-$R_9$ vicinal to one another taken together may form a ring, which is an optionally substituted $C_5$-$C_{20}$ cyclic hydrocarbyl group optionally substituted with one or more heteroatom-containing functional groups that do not interfere to any substantial degree with the catalytic process in which said complex may be employed; and $R_6$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_7$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{10}$ is hydrogen a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_9$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_4$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{11}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{12}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; $R_{15}$ is hydrogen, a hydrocarbyl containing 1 to 20 carbon and hydrogen atoms and optionally substituted with one or more heteroatom-containing functional groups that do not interfere to any substantial degree with the catalytic process in which said complex may be employed, a functional group other than said hydrocarbyl group which does not interfere to any substantial degree with the catalytic process in which said complex may be employed, or taken together with $R_{14}$ to form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed or with $R_5$ to form a ring which is an optionally substituted $C_6$-$C_{20}$ cyclic hydrocarbyl group optionally substituted with one or more heteroatom-containing functional groups that do not interfere to any substantial degree with the catalytic process in which said complex may be employed; provided that $R_{13}$ and at least one of $R_{12}$ and $R_{14}$ are independently selected from optionally substituted $C_1$-$C_{20}$ alkyl, optionally substituted $C_4$-$C_{20}$ alkyloxy, halogen and optionally substituted $C_5$-$C_{20}$ aryl, or $R_{13}$ taken together with $R_{12}$ or $R_{14}$ form a ring which is an optionally substituted $C_5$-$C_{20}$ cyclic hydrocarbyl group optionally substituted with one or more heteroatom-containing functional groups that do not interfere to any substantial degree with the catalytic process in which said complex may be employed, and provided that at least one of $R_{12}$, $R_{13}$ and $R_{14}$ is optionally substituted $C_4$-$C_{20}$ alkyloxy;

M is a transition metal atom;

n matches the formal oxidation state of the transition metal atom M;

X is halide, optionally substituted hydrocarbyl, alkoxide, amide, or hydride;

$NC^-$ is a non-coordinating anion; and p+q matches the formal oxidation state of the transition metal atom M;

(b)(i) in the case when a bis-arylimine pyridine $MX_n$ complex is present, (1) a co-catalyst compound capable of abstracting an anion and transferring a hydrocarbyl or hydride group to the transition metal atom, or (2) a co-catalyst compound capable of abstracting an anion and a co-catalyst compound capable of transferring a hydrocarbyl or hydride group to the transition metal atom; and/or (b)(ii) in the case where a [bis-arylimine pyridine $MX_p^+$] $[NC^-]_q$ complex is present, a co-catalyst compound capable of transferring a hydrocarbyl or hydride group to the transition metal atom.

* * * * *